United States Patent
Sugiki et al.

(10) Patent No.: US 9,000,208 B2
(45) Date of Patent: *Apr. 7, 2015

(54) GLUTAMATE DERIVATIVES OR SALTS THEREOF

(71) Applicant: Ajinomoto Co., Inc., Tokyo (JP)

(72) Inventors: Masayuki Sugiki, Kawasaki (JP); Toru Okamatsu, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 43 days.

This patent is subject to a terminal disclaimer.

(21) Appl. No.: 13/624,254

(22) Filed: Sep. 21, 2012

(65) Prior Publication Data

US 2013/0017603 A1  Jan. 17, 2013

Related U.S. Application Data

(63) Continuation of application No. PCT/JP2011/057932, filed on Mar. 23, 2011.

(30) Foreign Application Priority Data

Mar. 24, 2010 (JP) ................. 2010-067937

(51) Int. Cl.
*C07C 69/74* (2006.01)
*C07F 9/38* (2006.01)
*C07C 237/04* (2006.01)
*C07F 9/40* (2006.01)
*C07C 309/51* (2006.01)

(52) U.S. Cl.
CPC ............. *C07C 309/51* (2013.01); *C07F 9/3834* (2013.01); *C07C 237/04* (2013.01); *C07F 9/4021* (2013.01)

(58) Field of Classification Search
CPC ... C07C 237/04; C07C 309/51; C07F 9/3834; C07F 9/4021
USPC ........ 560/13, 19, 34, 41, 1; 564/123; 435/375
See application file for complete search history.

(56) References Cited

U.S. PATENT DOCUMENTS

| 4,087,331 | A | 5/1978 | Bucolo et al. |
| 5,354,753 | A | 10/1994 | Ohi et al. |
| 5,403,843 | A | 4/1995 | Akimoto et al. |
| 2007/0027106 | A1 | 2/2007 | Zerkowski et al. |
| 2009/0062366 | A1 | 3/2009 | Hachiya et al. |
| 2011/0028394 | A1 | 2/2011 | Karim et al. |
| 2011/0251418 | A1 | 10/2011 | Sugiki et al. |
| 2012/0101039 | A1 | 4/2012 | Fenscholdt et al. |
| 2012/0122784 | A1 | 5/2012 | Norremark et al. |
| 2012/0129926 | A1 | 5/2012 | Norremark |
| 2013/0017603 | A1 | 1/2013 | Sugiki et al. |
| 2013/0072491 | A1 | 3/2013 | Yasuda et al. |
| 2013/0102570 | A1 | 4/2013 | Yasuda et al. |
| 2013/0237702 | A1 | 9/2013 | Sugiki et al. |

FOREIGN PATENT DOCUMENTS

| EP | 1 882 684 | | 1/2008 |
| EP | 2 546 231 | | 1/2013 |
| EP | 2 554 165 | | 2/2013 |
| JP | EP0530537 | A1 * | 10/1993 |
| JP | 06-016558 | | 1/1994 |
| JP | 06-49069 | | 2/1994 |
| JP | 06-172287 | | 6/1994 |
| WO | 92/03436 | A1 | 3/1992 |
| WO | 2007/055388 | | 5/2007 |
| WO | 2007/055393 | | 5/2007 |
| WO | 2010/136035 | | 12/2010 |
| WO | 2010/136036 | | 12/2010 |
| WO | 2010/136037 | | 12/2010 |
| WO | 2011/014707 | | 2/2011 |

OTHER PUBLICATIONS

Miyamoto et al. (Agonistic Action of Synthetic Analogues of Quisqualic Acid at the Insect Neuromuscular Junction, Archives of Insect Biochemistry and Physiology 2, pp. 65-73, 1985).*
Gould (Salt selection for basic drugs, International Journal of Pharmaceutics, 33, pp. 201-217, 1986).*
(SparkPeople, 2013, downloaded from internet Mar. 7, 2014).*
(Mayo Clinic, 2013, downloaded from the internet on Mar. 7, 2014).*
(WebMD, 2013, downloaded from Internet on Mar. 7, 2014).*
Gould (International Journal of Pharmaceutics, vol. 33, pp. 201-217, 1986).*
Gabor Szasz, "Clinical Chemistry", vol. 22, No. 12 (1976) pp. 2051-2055.
R. Lloyd et al, "Journal of Medicinal Chemistry", vol. 8, No. 3 (1965) pp. 398-400.
S. Bashir et al., "Analytica Chimica Acta", vol. 519, No. 2, (2004) pp. 181-187.
M. Wang et al., "Journal of Biological Chemistry", vol. 281, No. 13 (2006) pp. 8864-8870.
T. Ohsu et al., "Journal of Biological Chemistry", vol. 285, No. 2 (2010) pp. 1016-1022.
Matsuoka, H. et al., "Chemical & Pharmaceutical Bulletin", vol. 45, No. 7 (1997), pp. 1146-1150.
Kraut L. et al., "Phytochemistry", vol. 45, No. 8 (1997) pp. 1621-1626.
International Search Report issued in PCT/JP2011/057932 on Jun. 21, 2011.
Written Opinion issued in PCT/JP2011/057932 on Jun. 21, 2011.
European Search Report in Application No. 11759645.2 issued Dec. 13, 2013.
Itoh et al., Chem. Pharm. Bull. vol. 44, No. 8, (1996) pp. 1498-1509.
Kraut et al., Phytochemistry, vol. 45, No. 8, (1997) pp. 1621-1626.
U.S. Appl. No. 14/229,152, filed Mar. 28, 2014, Sugiki, et al.
U.S. Appl. No. 13/600,977, filed Aug. 31, 2012, Sugiki, et al.
U.S. Appl. No. 13/630,562, filed Sep. 28, 2012, Yasuda, et al.
Office Action dated Nov. 25, 2014 issued in corresponding Japanese patent application No. 2012-507126 with English translation.

* cited by examiner

*Primary Examiner* — Brandon Fetterolf
*Assistant Examiner* — Blaine G Doletski
(74) *Attorney, Agent, or Firm* — Oblon, McClelland, Maier & Neustadt, L.L.P.

(57) ABSTRACT

Compounds having an excellent CaSR agonist activity are in demand. The invention provides glutamate derivatives or salts thereof, pharmaceutical compositions comprising the glutamate derivatives, preventive or therapeutic agents for diarrhea, hyperparathyroidism or peptic ulcer.

18 Claims, 2 Drawing Sheets

GLUTAMATE DERIVATIVES OR SALTS THEREOF

CROSS REFERENCES TO RELATED APPLICATIONS

This application is a Continuation of International Application No. PCT/JP2011/057932, filed on Mar. 23, 2011, and claims priority to Japanese Patent Application No. 2010-067937, filed on Mar. 24, 2010.

TECHNICAL FIELD

The present invention relates to glutamate (glutamic acid ester) derivatives having a CaSR agonist activity or pharmaceutically acceptable salts thereof; and CaSR agonist agents, pharmaceutical compositions, preventive or therapeutic agents for diarrhea, preventive or therapeutic agents for peptic ulcer, preventive or therapeutic agents for hyperparathyroidism and kokumi-imparting agents, each of which comprises as an active ingredient the glutamate derivative or pharmaceutically acceptable salts thereof.

BACKGROUND ART

A calcium sensing receptor (CaSR) is also called a calcium receptor, and such receptor signals regulate various in vivo functions. Thus, there is a possibility that substances having a CaSR agonist activity are useful for treating or preventing various diseases and also useful as kokumi-imparting agents. Patent Document 1 discloses a screening method for a kokumi-imparting substance and a kokumi-imparting agent containing a kokumi-imparting substance obtained by the screening method. In the document it is found that a variety of low molecular weight peptides have the CaSR agonist activity. It is disclosed therein that based on this finding, it has become possible to provide a kokumi-imparting agent which can impart "kokumi", the taste that cannot be expressed only with five basic tastes of sweet, salty, sour, bitter and umami tastes, and the taste that enhances marginal tastes of the basic tastes described above, such as thickness, growth (mouthfulness), continuity and harmony.

On the other hand, it has been known from old that γ-glutamylanilide derivatives act as the substrate for γ-glutamyltransferase, and can be used for enzyme activity measurements (Non-Patent Document 1, Patent Document 2). However, there is no publication that describes the relation of "the calcium sensing receptor (CaSR) or G protein-coupled receptor," which is a characteristic feature of the present invention, to "kokumi taste," "diarrhea" or "hyperparathyroidism." Also in some known compounds of γ-glutamylanilide derivatives which are 3-sulfonic acids, 3-carboxylic acids and 3-nitro derivatives, most of their utilities are focused on substrates in enzyme activity measurements of γ-glutamyltransferase, and use as antibacterial agents or antiallergic agents (Non-Patent Document 2 and Patent Document 3) and use as analysis reagents for mass spectrometry (Non-Patent Document 3) are only known for other uses. Furthermore, Cinacalcet and analogous synthetic low molecular weight compounds and γ-glutamylpeptide derivatives including glutathione are known as CaSR-activating compounds (Patent Document 4 and Non-Patent Documents 4 and 5), but these compounds are structurally different from the glutamate derivatives of the present invention.

Therefore, it is expected to provide more excellent kokumi-imparting agents by searching more varieties of compounds having the CaSR agonist activity. It is also expected to provide CaSR agonist agents, pharmaceutical compositions and preventive or therapeutic agents for diarrhea.

Patent Documents

[Patent Document 1] WO 2007/055393A1
[Patent Document 2] U.S. Pat. No. 4,087,331
[Patent Document 3] JPA H06-172287
[Patent Document 4] WO 2007/055388A2

Non-Patent Documents

[Non-Patent Document 1] Clinical Chemistry, 22, 2051 (1976)
[Non-Patent Document 2] Journal of Medicinal Chemistry (1965), 8 (3), 398-400
[Non-Patent Document 3] Analytica Chimica Acta (2004), 519 (2), 181-187
[Non-Patent Document 4] Journal of Biological Chemistry (2006), 281 (13), 8864-70
[Non-Patent Document 5] Journal of Biological Chemistry, (2010), 285 (2), 1016-22

DISCLOSURE OF THE INVENTION

Problems to be Solved by the Invention

An object of the present invention is to search various types of compounds having the CaSR agonist activity and provide CaSR agonist agents, pharmaceutical compositions, preventive or therapeutic agents for diarrhea, therapeutic agents for small intestine inflammation and preventive or therapeutic agents for hyperparathyroidism as well as kokumi-imparting agents, each comprising the compounds.

Means for Solving the Problems

As a result of search for compounds having the CaSR agonist activity, surprisingly the inventors found that various γ-glutamate derivatives and analogues thereof (hereinafter referred to as "glutamate derivatives") have an excellent CaSR agonist activity. They also found that the glutamate derivatives having the CaSR agonist activity or pharmaceutically acceptable salts thereof can be useful CaSR agonist agents, pharmaceutical compositions, preventive or therapeutic agents for hyperparathyroidism, peptic ulcer or diarrhea, associated with CaSR for their pathological conditions, or kokumi-imparting agents. The present invention has thus been accomplished based on these findings.

That is, the present invention provides the following features.

[1] A glutamate derivative of formula (I):

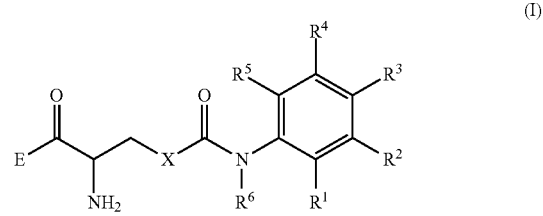

(wherein:
$R^1$, $R^2$, $R^3$, $R^4$ and $R^5$ each independently is a group selected from hydrogen atom, a halogeno group, hydroxyl group, nitro group, amino group, a $C_{1-6}$ alkyl group which may have a substituent(s), a $C_{1-6}$ alkoxy group which may have a substituent(s), a mono- or di-$C_{1-6}$ alkylamino group which may have a substituent(s), sulfo group, and a group:

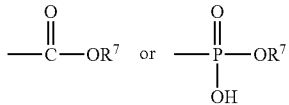

provided that either one of $R^1$, $R^2$ and $R^3$ is sulfo group or a group selected from:

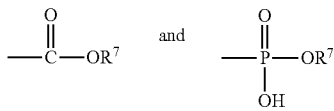

$R^6$ is hydrogen atom, hydroxyl group or a $C_{1-6}$ alkyl group which may have a substituent(s);
$R^7$ is hydrogen atom or a $C_{1-6}$ alkyl group which may have a substituent(s);
X is methylene group or oxygen atom; and,
E is a $C_{1-6}$ alkoxyl group which may have a substituent(s), a mercapto group which may have a substituent(s), or a group:

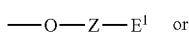

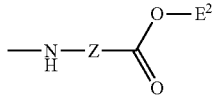

(wherein:
Z is a divalent $C_{1-6}$ hydrocarbon group which may have a substituent(s), $E^1$ is a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), $E^2$ is hydrogen atom or a $C_{1-6}$ alkyl group, and Z and $E^1$ may be combined together to form a ring)), or a pharmaceutically acceptable salts thereof.

[1-2] The glutamate derivative represented by the aforesaid general formula (I) or pharmaceutically acceptable salt thereof, according to [1] above, wherein:
$R^1$, $R^2$, $R^3$, $R^4$ and $R^5$ each independently is a group selected from hydrogen atom, a halogeno group, hydroxyl group, nitro group, amino group, a $C_{1-6}$ alkyl group which may have a substituent(s), a $C_{1-6}$ alkoxy group which may have a substituent(s) or a mono- or di-$C_{1-6}$ alkylamino group which may have a substituent(s), sulfo group or a group:

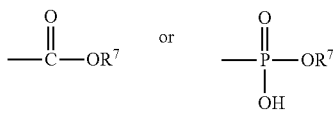

provided that either one of $R^1$, $R^2$ and $R^3$ is sulfo group or a group selected from sulfo group or a group:

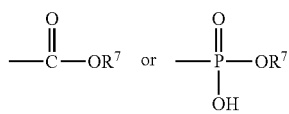

$R^6$ is hydrogen atom, hydroxyl group or a $C_{1-6}$ alkyl group which may have a substituent(s);
$R^7$ is hydrogen atom, hydroxyl group or a $C_{1-6}$ alkyl group which may have a substituent(s);
X is methylene group or oxygen atom; and,
E is a $C_{1-6}$ alkoxy group which may have a substituent(s), a mercapto group which may have a substituent(s), or a group;

(wherein Z is a divalent $C_{1-6}$ hydrocarbon group which may have a substituent(s) and $E^2$ is hydrogen atom or a $C_{1-6}$ alkyl group);
provided that:
when E is methoxy group, ethoxy group or benzyloxy group and X is methylene group, in a group:

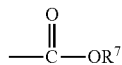

$R^7$ is not methyl group, ethyl group or benzyl group; and,
when E is butoxy group and X is methylene group, in a group:

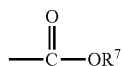

$R^7$ is not a group:

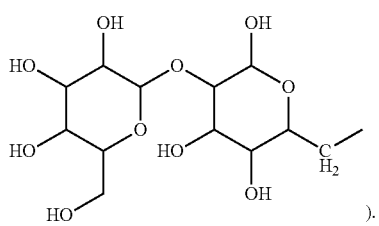

[1-3] The glutamate derivative or pharmaceutically acceptable salt thereof, according to [1] or [1-2] above, wherein in general formula (I) E is a $C_{1-6}$ alkoxy group or a group:

-OZ-$E^1$                             (IIa)

(in formula (IIa), Z is a divalent $C_{1-6}$ hydrocarbon group which may have a substituent(s), $E^1$ is a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), or, Z and $E^1$ may be combined together to form a ring).

[2] A glutamate derivative represented by general formula (I) above (wherein:

$R^1$, $R^2$, $R^3$, $R^4$ and $R^5$ each independently is a group selected from hydrogen atom, a halogeno group, hydroxyl group, nitro group, amino group, a $C_{1-6}$ alkyl group which may have a substituent(s), a $C_{1-6}$ alkoxy group which may have a substituent(s) or a mono- or di-$C_{1-6}$ alkylamino group which may have a substituent(s), sulfo group, and a group:

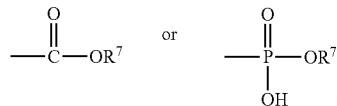

provided that at least one of $R^1$, $R^2$ or $R^3$ is sulfo group or a group selected from:

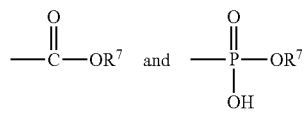

$R^6$ is hydrogen atom, hydroxyl group or a $C_{1-6}$ alkyl group which may have a substituent(s);

$R^7$ is hydrogen atom or a $C_{1-6}$ alkyl group which may have a substituent(s);

X is methylene group or oxygen atom; and,

E is a $C_{1-6}$ alkoxyl group which may have a substituent(s), a mercapto group which may have a substituent(s), or a group:

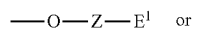

(IIa)

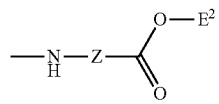

(IIb)

(in formulae (IIa) and (IIb), Z represents a divalent $C_{1-6}$ hydrocarbon group which may have a substituent(s), $E^1$ represents a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s), or a carbamoyl group which may have a substituent(s), $E^2$ represents hydrogen atom or a $C_{1-6}$ alkyl group; or Z and $E^1$ may be combined together to form a ring); provided that:

(i) when X is methylene group, $R^3$ is a carboxylic acid group and $R^1$, $R^2$, $R^4$, $R^5$ and $R^6$ are hydrogen atom, then, E is not methoxy group, and, (ii) when X is methylene group, $R^2$ is a carboxylic acid group, $R^5$ is fluorine atom and $R^1$, $R^3$, $R^4$ and $R^6$ are hydrogen atom, then, E is not methoxy group); or pharmaceutically acceptable salts thereof.

[2-2] The glutamate derivative represented by general formula (I) or pharmaceutically acceptable salt thereof, according to [2] above (wherein:

$R^1$, $R^2$, $R^3$, $R^4$ and $R^5$ each independently is a group selected from hydrogen atom, a halogeno group, hydroxyl group, nitro group, amino group, a $C_{1-6}$ alkyl group which may have a substituent(s), a $C_{1-6}$ alkoxy group which may have a substituent(s) or a mono- or di-$C_{1-6}$ alkylamino group which may have a substituent(s), sulfo group, and a group:

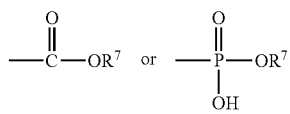

provided that at least one of $R^1$, $R^2$ and $R^3$ is sulfo group or a group selected from:

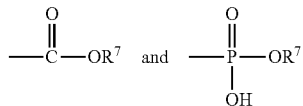

$R^6$ is hydrogen atom, hydroxyl group or a $C_{1-6}$ alkyl group which may have a substituent(s);

$R^7$ is hydrogen atom or a $C_{1-6}$ alkyl group which may have a substituent(s);

X is methylene group or oxygen atom; and,

E is a group selected from a $C_{1-6}$ alkoxy group which may have a substituent(s), a mercapto group which may have a substituent(s) or a group:

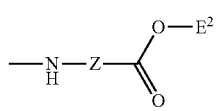

(IIb)

(in formula (IIb), Z represents a divalent $C_{1-6}$ hydrocarbon group which may have a substituent(s) and $E^2$ represents hydrogen atom or a $C_{1-6}$ alkyl group);

provided that (i) when X is methylene group, $R^3$ is a carboxylic acid group and $R^1$, $R^2$, $R^4$, $R^5$ and $R^6$ are hydrogen atom, then, E is not methoxy group;

(ii) when X is methylene group, $R^2$ is a carboxylic acid group, $R^5$ is fluorine atom and $R^1$, $R^3$, $R^4$ and $R^6$ are hydrogen atom, then, E is not methoxy group; and, (iii) when E is methoxy group, ethoxy group or benzyloxy group and X is methylene group, then, in a group:

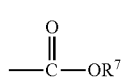

$R^7$ is not methyl group, ethyl group or benzyl group;

when E is butoxy group and X is methylene group, $R^7$ is not the following group:

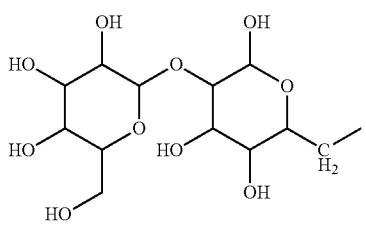 [SMILES: CCC1OC(O)C(OC2OC(CO)C(O)C(O)C2O)C(O)C1O]

in a group:

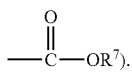

[2-3] The glutamate derivative or pharmaceutically acceptable salt thereof, according to any one of [1-2] and [2-2] above, wherein:

E is a $C_{1-6}$ alkoxy group which may have a substituent(s) or a group:

$$-O-Z-E^1 \quad (IIa)$$

(in formula (IIa), Z represents a divalent $C_{1-6}$ hydrocarbon group which may have a substituent(s), $E^1$ represents a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), or Z and $E^1$ may be combined together to form a ring).

[3] A pharmaceutical composition, a CaSR agonist agent, a preventive or therapeutic agent for diarrhea, a preventive or therapeutic agent for hyperparathyroidism, a preventive or therapeutic agent for peptic ulcer or a kokumi-imparting agent, comprising a glutamate derivative represented by general formula (I) above (wherein:

$R^1$, $R^2$, $R^3$, $R^4$ and $R^5$ each independently is a group selected from hydrogen atom, a halogeno group, hydroxyl group, nitro group, amino group, a $C_{1-6}$ alkyl group which may have a substituent(s), a $C_{1-6}$ alkoxy group which may have a substituent(s), a mono- or di-$C_{1-6}$ alkylamino group which may have a substituent(s), sulfo group, and a group:

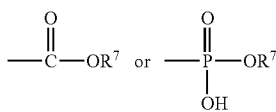

provided that at least one of $R^1$, $R^2$ and $R^3$ is a group selected from sulfo group or a group:

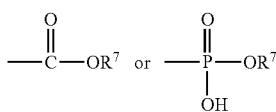

$R^6$ is hydrogen atom, hydroxyl group or a $C_{1-6}$ alkyl group which may have a substituent(s);

$R^7$ is hydrogen atom or a $C_{1-6}$ alkyl group which may have a substituent(s);

X is methylene group or oxygen atom; and,

E is a $C_{1-6}$ alkoxy group which may have a substituent(s), a mercapto group which may have a substituent(s) or a group:

 (IIa)

 (IIb)

(wherein:

Z is a divalent $C_{1-6}$ hydrocarbon group which may have a substituent(s), $E^1$ is a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), $E^2$ is hydrogen atom or a $C_{1-6}$ alkyl group, and Z and $E^1$ may be combined together to form a ring)); or a pharmaceutically acceptable salt thereof

[4] A pharmaceutical composition, a CaSR agonist agent, a preventive or therapeutic agent for diarrhea, a preventive or therapeutic agent for hyperparathyroidism, a preventive or therapeutic agent for peptic ulcer or a kokumi-imparting agent, comprising the glutamate derivative or pharmaceutically acceptable salts thereof according to any one of [1] to [2-2].

Effects of the Invention

According to the present invention, various compounds having an excellent CaSR agonist activity can be provided and CaSR agonist agents and pharmaceutical compositions, especially, therapeutic agents for hyperparathyroidism, preventive or therapeutic agents for diarrhea and peptic ulcer as well as condiments and kokumi-imparting agents.

BEST MODE FOR CARRYING OUT THE INVENTION

Figure 1:
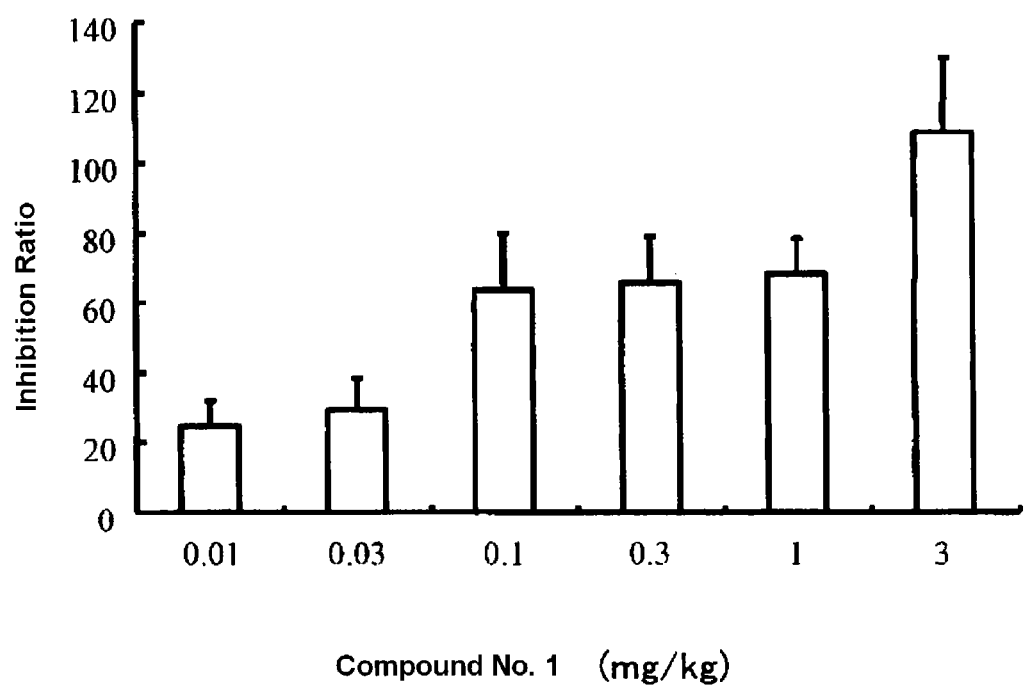
FIG. 1 shows the preventive activity of Reference Compound No. 1 against diarrhea.

Hereinafter the present invention is described in detail.

As used herein, the "$C_{1-6}$ alkyl group" is intended to mean a monovalent group derived by removing one optional hydrogen atom from a straight or branched aliphatic hydrocarbon having 1 to 6 carbon atoms. Specific examples are groups such as methyl, ethyl, isopropyl, butyl, n-butyl, isobutyl, sec-butyl, t-butyl, pentyl, isopentyl, 2,3-dimethylpropyl, hexyl, etc., preferably, a $C_{1-3}$ alkyl group.

The "$C_{1-6}$ alkoxy group" is intended to mean a $C_{1-6}$ alkyl-O—. Specific examples include groups such as methoxy, ethoxy, 1-propoxy, 2-propoxy, n-butoxy, i-butoxy, sec-butoxy, t-butoxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy, 3-hexyloxy, etc., preferably, a $C_{1-3}$ alkoxy group.

The halogeno group includes fluorine atom, chlorine atom, bromine atom and iodine atom.

The mono- or di-$C_{1-6}$ alkylamino group means an amino group derived by substituting 1 or 2 hydrogen atoms with the $C_{1-6}$ alkyl group described above. Specific examples include groups such as methylamino, dimethylamino, ethylamino, diethylamino, etc., preferably, a mono- or di-$C_{1-3}$ alkylamino group.

The "$C_{1-6}$ acyloxy group" is intended to mean a group shown by a $C_{1-6}$ alkyl-C(O)—O—, a $C_{3-6}$ cycloalkyl-C(O)—O— or phenyl-C(O)—O—. Herein, the $C_{3-6}$ cycloalkyl group includes a group such as cyclopropyl, cyclopentyl, cyclohexyl, etc. The $C_{1-6}$ acyloxy group includes a group such as acetyloxy, propionyloxy, cyclohexylcarbonyloxy, benzoyloxy, etc., preferably, a $C_{1-6}$ alkyl-C(O)—O—, and more preferably, a $C_{1-3}$ alkyl-C(O)—O—.

The "$C_{1-6}$ alkoxycarbonyl group" is intended to mean a group shown by $C_{1-6}$ alkyl-O—C(O)— and includes a group such as methoxycarbonyl, ethoxycarbonyl, etc., preferably, a $C_{1-3}$ alkoxycarbonyl group.

The "$C_{1-6}$ alkoxycarbonyloxy group" is intended to mean a group shown by a $C_{1-6}$ alkyl-O—C(O)—O— and includes a group such as methoxycarbonyloxy, ethoxycarbonyloxy, etc., preferably, a $C_{1-3}$ alkoxycarbonyloxy group.

The "aryl group" is intended to mean an aromatic hydrocarbon ring group such as phenyl, naphthyl, etc., preferably, phenyl group.

The "heteroaryl group" is intended to mean a 5-membered to 10-membered aromatic heterocyclic group containing 1, 2 or 3 hetero atoms selected from N, S and O. Specific examples of the aromatic hetero ring include a group such as pyridine, pyridazine, pyrazine, pyrimidine, thiazole, isothiazole, oxazole, isoxazole, oxadiazole, pyrazole, imidazole, furan, thiophen, pyrrole, etc., preferably, pyridine, imidazole, thiophen, oxadiazole, indole, etc. Preferred is a 5-membered to 6-membered aromatic hetero ring and specific examples are groups including pyridine, pyrimidine, etc.

The "divalent $C_{1-6}$ hydrocarbon group" is intended to mean a divalent group derived by removing optional two hydrogen atoms from a straight or branched aliphatic hydrocarbon having 1 to 6 carbon atoms and containing 1 to several double bonds or triple bonds. Specific examples are groups including methylene, ethane-1,1-diyl, vinylene, ethynylene, propargyl, etc.

In E, the "ring" formed by combining Z and $E^1$ together when E is shown by formula (IIa) is intended to mean a saturated or unsaturated 5- or 6-membered ring containing Z-$E^1$ as a part of the ring, which may further contain as the ring-forming atom(s) 1 to 3 hetero atoms selected from nitrogen atom, oxygen atom and sulfur atom and which may further be condensed with a benzene ring. Preferably, the ring is a saturated or unsaturated 5- or 6-membered ring which may contain 1 to 3 oxygen atoms as the ring-forming atoms. Examples of E when Z and $E^1$ are combined together to form the ring include the following groups.

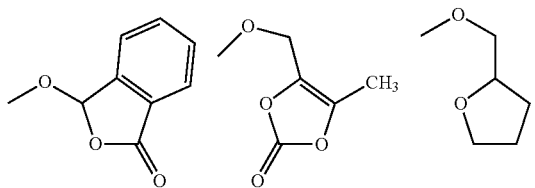

The groups shown by E-CO— described above can also function as a carboxyl group which is modified to form a prodrug converted into a carboxyl group in vivo, as described in, e.g., Prog. Med. 5: 2157-2161 (1985), IYAKUHIN-NO-KAIHATSU (Development of Drugs) (published by Hirokawa Shoten in 1990), volume 7, Bunshi Sekkei (Molecule Design), p. 163-198, or SAISHIN SOYAKU-KAGAKU (Recent Innovative Drug Chemistry) (published by Technomics, Inc. in 1999), last volume, p. 271-298.

In the glutamate derivative of the present invention of general formula (I) of the present invention described above, it is preferred that $R^1$, $R^2$, $R^3$, $R^4$ and $R^5$ each independently is a group selected from hydrogen atom, a halogeno group, hydroxyl group, nitro group, amino group, a $C_{1-3}$ alkyl group which may have a substituent(s), a $C_{1-3}$ alkoxy group which may have a substituent(s), and a mono- or di-$C_{1-3}$ alkylamino group which may have a substituent(s). More preferably, $R^1$, $R^2$, $R^3$, $R^4$ and $R^5$ each independently is a group selected from hydrogen atom, chloro or bromo group, hydroxyl group, nitro group, amino group, methyl group or methoxy group.

In $R^1$, $R^2$, $R^3$, $R^4$ and $R^5$, either one of $R^1$, $R^2$ and $R^3$ is preferably sulfo group or a group selected from:

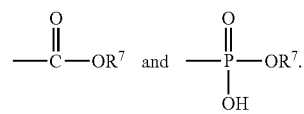

On the other hand, $R^1$, $R^2$, $R^3$, $R^4$ and $R^5$ each independently represents a group selected from hydrogen atom, a halogeno group, hydroxyl group, nitro group, amino group, a $C_{1-3}$ alkyl group which may have a substituent(s), a $C_{1-3}$ alkoxy group which may have a substituent(s), and a mono- or di-$C_{1-3}$ alkylamino group which may have a substituent(s). More preferably, $R^1$, $R^3$, $R^4$ and $R^5$ each independently represents a group selected from hydrogen atom, chloro or bromo group, hydroxyl group, nitro group, amino group, methyl group and methoxy group.

In the above general formula (I) of the present invention, $R^2$ is preferably sulfo group, a carboxylic acid group or a phosphonic acid group.

Alternatively, either one of $R^1$ and $R^3$ may be sulfo group and in this case, preferably $R^4$ may also be a halogeno group.

In the above general formula (I) of the present invention, preferably $R^6$ and $R^7$ each independently represents hydrogen atom or methyl group. More preferably, $R^6$ is hydrogen atom or methyl group and $R^7$ is hydrogen atom. Preferably, $R^6$ may also be hydroxyl group.

In the above general formula (I) of the present invention, X is preferably methylene group.

In general formula (I) of the present invention described above, preferably E is a group other than a group selected from the group consisting of t-butyloxy group and benzyloxy group.

In general formula (I) of the present invention described above, E is preferably a $C_{1-6}$ alkoxy group which may have a substituent(s), more preferably, a $C_{1-6}$ alkoxy group and particularly preferably, a $C_{1-3}$ alkoxy group.

When E is a $C_{1-6}$ alkoxy group which may have a substituent(s), E also preferably represents a group:

O-Z-$E^1$ (wherein:
Z is a divalent $C_{1-6}$ hydrocarbon group which may have a substituent(s), $E^1$ is a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), and Z and $E^1$ may be combined together to form a ring)).

In the glutamate derivative of the present invention, which is represented by formula (I) described above, or pharmaceutically acceptable salts thereof, either one of $R^1$, $R^2$ and $R^3$ is preferably sulfo group, a carboxylic acid group or a phosphonic acid group, and particularly preferably, sulfo group.

In particular, when $R^2$ is sulfo group in general formula (I) above, it is preferred that $R^1$ is hydrogen atom or hydroxyl group, $R^3$ is hydrogen atom, chloro group, hydroxyl group, methyl group or methoxy group, $R^4$ is hydrogen atom, chloro group or nitro group, $R^5$ is hydrogen atom, hydroxyl group, methyl group or methoxy group, $R^6$ is hydrogen atom or methyl group, and X is methylene group or oxygen atom. In general formula (I) above, when $R^2$ is sulfo group, it is most preferred that $R^1$ is hydrogen atom or hydroxyl group, $R^3$ is hydrogen atom, chloro group or methyl group, $R^4$ is hydrogen atom or chloro group, $R^5$ is hydrogen atom, hydroxyl group or methyl group, $R^6$ is hydrogen atom, and X is methylene group.

In the glutamate derivative of the present invention, which is represented by general formula (I) above, or pharmaceutically acceptable salts thereof, especially when $R^2$ is a carboxylic acid group in general formula (I) above, it is most preferred that $R^1$ is hydrogen atom or hydroxyl group, $R^3$ is hydrogen atom, $R^4$ is hydrogen atom or bromo group, $R^5$ is hydrogen atom, $R^6$ is hydrogen atom, and X is methylene group or oxygen atom.

In the glutamate derivative of the present invention, which is represented by general formula (I) above, or pharmaceutically acceptable salts thereof, especially when $R^2$ is a-PO(OCH$_3$)OH group or —PO(OH)$_2$ group, it is most preferred that $R^1$ is hydrogen atom, $R^3$ is hydrogen atom, $R^4$ is hydrogen atom, $R^5$ is hydrogen atom, $R^6$ is hydrogen atom, and X is methylene group.

In the glutamate derivative of the present invention represented by general formula (I) above, the compounds described in EXAMPLES are particularly preferred and the compounds described in REFERENCE EXAMPLES 1, 7, 10, 21, 22, 24, 32, 33, 34, 35 and 37, in which the carboxyl group in the amino acid moiety is substituted with a $C_{1-6}$ alkoxycarbonyl group, are also preferred. Particularly preferred are the compounds described in REFERENCE EXAMPLES 7, 10, 21, 22, 24, 32, 33, 34, 35 and 37, which are substituted as described above.

In general formula (I) described above, the alkyl group, alkoxy group and mono- or di-alkylamino group each may have a substituent(s) and the substituent includes, but is not limited to, a halogen, hydroxy group, an alkoxy group, amino group, a mono- or di-alkylamino group, carboxyl group and sulfo group. Also, the alkoxy group and mono- or di-alkylamino group, which are the substituents, each preferably is a lower alkoxy group or a lower mono- or di-alkylamino group. As used herein, the term lower is intended to mean 1 to 3 carbon atoms in the whole substituent.

The glutamate derivative of the present invention represented by general formula (I) above may be may be in the form of pharmaceutically acceptable salts thereof. The pharmaceutically acceptable salts of the glutamate derivative of the present invention represented by general formula (I) above includes edible salts, and examples of the salts with acidic groups such as a carboxyl group, sulfo group, etc. in the formula are ammonium salts, salts with alkali metals such as sodium, potassium, etc., salts with alkaline earth metals such as calcium, magnesium, etc., aluminum salts, zinc salts, salts with organic amines such as triethylamine, ethanolamine, morpholine, pyrrolidine, piperidine, piperazine, dicyclohexylamine, etc., and salts with basic amino acids such as arginine, lysine, etc. When a basic group(s) exists in the formula (I), the salts with such basic groups include salts with inorganic acids such as hydrochloric acid, sulfuric acid, phosphoric acid, nitric acid, hydrobromic acid, etc., salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, malic acid, etc., and salts with organic sulfonic acids such as methane sulfonic acid, benzene sulfonic acid and p-toluene sulfonic acid.

As used herein, "CaSR" is intended to mean a calcium sensing receptor, and belongs to the class C family of seven transmembrane receptors. CaSR is also called a calcium receptor. As used herein, the term "CaSR agonist" is intended to mean a compound binding to the above CaSR to activate CaSR, and the term "CaSR agonist agent" is intended to mean an agent or a substance binding to the above CaSR to activate CaSR. As used herein, the term "activate CaSR" is intended to mean that a ligand binds to CaSR thereby to activate guanine nucleotide-binding proteins and transmit signals. The behavior that a compound binds to CaSR to activate CaSR is termed "CaSR agonistic activity."

A preferred example of the CaSR described above includes human CaSR encoded by human CaSR gene which is registered as GenBank Accession No. NM_000388. Meanwhile, CaSR is not limited to the protein encoded by the gene of the sequence described above and may be proteins encoded by the gene having 60% or more, preferably 80% or more, and more preferably 90% or more homology, to the sequence described above, as long as CaSR encodes proteins having the CaSR function. The CaSR function can be examined by expressing these genes in cells and measuring changes of current and changes of intracellular calcium ion level upon calcium addition.

The origin of CaSR described above is not particularly limited, and examples of CaSR include any animal-derived CaSR such as those of mouse, rat, canine, etc., in addition to the human CaSR.

The CaSR activity can be confirmed by using living cells expressing CaSR or its fragments, cell membranes expressing CaSR or its fragments, an in vitro system containing proteins of CaSR or its fragments.

An example using living cells is given below but the activity confirmation is not limited thereto.

CaSR is expressed in culture cells of *Xenopus* oocytes, hamster ovary cells, human embryonic kidney cells, etc. The expression is enabled by cloning a CaSR gene to a plasmid bearing a foreign gene, and then introducing cRNA in the plasmid state or cRNA generated from the plasmid template. The reaction can be detected by electrophysiological means, or using a fluorescence indicator for detecting an increase of intracellular calcium.

The expression of CaSR is first confirmed in a response by calcium or a specific activator. Oocytes wherein the intracellular current was observed or culture cells wherein fluorescence from a fluorescence indicator was observed are used for calcium of approximately 5 mM concentration. Concentration dependence is monitored by varying the concentration of calcium. Next, a test substance is prepared to become 1 μM to 1 mM, which is added to oocytes or culture cells. Then, CaSR activity is determined in the presence of the test substance to determine the CaSR agonistic activity of the test substance described above.

The glutamate derivative of the present invention (hereinafter also referred to as the compound of the present invention) can be used as a medicament, in particular, as the CaSR agonist agent, and can be used as a preventive or therapeutic agent for diseases which are improved by activation of CaSR.

CaSR is expressed in various tissues and plays various physiological activities. CaSR has an activity of sensing an increase of blood calcium level in the parathyroid and suppressing the secretion of parathyroid hormone (PTH) to restore the blood calcium level. Accordingly, compounds capable of activating CaSR are expected to be therapeutic agents for various diseases, in addition to hyperparathyroidism described above, including bone diseases and upper and lower gastrointestial diseases (The Journal of Clinical Investigation, 1997, vol. 99, p. 2328-2333 and The American Journal of Physiology-Gastrointestinal and Liver Physiology, 2002, vol. 283, p. G240-G250), diabetes mellitus (The Journal of Biological Chemistry, 1999, vol. 274, p. 20561-20568 and The Journal of Biological Chemistry, 2000, vol. 275, p. 18777-18784), hypopituitarism/hyperpituitarism (Molecular Endocrinology, 1996, vol. 10, p. 555-565), etc.

In addition to calcium regulation, it is reported that CaSR is expressed in adipocytes, along with mature adipocytes and undifferentiated adipocytes and involved in differentiation suppression (Endocrinology. 2005 May; 146 (5):2176-9, Exp Cell Res. 2004 Dec. 10; 301 (2):280-92), expressed in erythroblasts, megakaryocytes and platelets in bone marrow cells and associated with hemopoietic regulation (J. Bone Miner. Res. 1997 December; 12 (12):1959-70), and expressed in gastric parietal cells and involved in gastric acid secretion (J. Clin. Endocrinol. Metab. 2005 March; 90 (3):1489-94.)

In addition to the tissues above, CaSR is expressed in the duodenum, jejunum and ileum (Am. J. Physiol. Gastrointest. Liver Physiol. 2002 July; 283 (1):G240-50), large intestine (Am. J. Physiol. Gastrointest. Liver Physiol. 2002 July; 283 (1):G240-50), epidermal keratinocyte (Cell Calcium 2004 March; 35 (3):265-73), hepatocytes (J. Biol. Chem. 2001 Feb. 9; 276 (6):4070-9), epithelium lentis (Biochem. Biophys. Res. Commun. 1997 Apr. 28; 233 (3):801-5), Langerhans islet β cells (Endocrine 1999 December; 11 (3):293-300), lung (J. Clin. Endocrinol. Metab. 1998 February; 83 (2):703-7), monocytic cells (J. Clin. Invest. 2000 May; 105 (9):1299-305), osteoblasts (Endocrinology. 2004 July; 145 (7):3451-62, Am. J. Physiol. Endocrinol. Metab. 2005 March; 288 (3): E608-16. Epub 2004 Nov. 16), etc., suggesting that it is involved in the regulation of functions in these tissues.

It is also confirmed that glutathione known as a kokumi-imparting agent has a calcium receptor activation activity and a peptide derivative having a CaSR agonist activity produces a kokumi taste (WO 2007/055393). Thus, the compounds having the CaSR agonist activity are shown to be useful as kokumi-imparting agents.

In particular, a calcium receptor is expressed in gastric G cells and parietal cells, and has been found to have the activity of stimulating gastrin and gastric acid secretion (Journal of Clinical Investigation (1997), 99: 2328-2333, Gastroenterology 1999; 116: 118-126). Also, the function of the calcium receptor in the gastrointestinal tract (World J. Gastroenterol. 2006; 12 (20): 3229-3236) and expression of the calcium receptor in the large intestine to modulate fluid secretion are reported (The American Journal of Physiology-Gastrointestinal and Liver Physiology (2002), 283: G240-G250), etc. Furthermore, calcimimetics including Cinacalcet, γ-glutamylpeptide derivatives, etc. have an inhibitory effect on an animal model of diarrhea (WO 2008/139947), an effect of promoting bicarbonate secretion or an activity of promoting somatostatin secretion, and an effect of reducing the damage area in an animal model of enteritis induced by non-steroidal anti-inflammatory drugs (NSAID (WO 2009/119554). Thus, compounds having a CaSR agonist activity are shown to be useful as preventive or therapeutic agents for acid secretion-associated disease such as diarrhea, gastric ulcer, duodenal ulcer, reflux esophagitis, etc., or as appetite regulators.

Therefore, the compound of the present invention can be used as the active ingredient of a pharmaceutical composition for the prevention or treatment of diseases that are improved by activation of CaSR.

As used herein, the "diseases that are improved by activation of CaSR" are intended to mean a disease or incompetence characterized by abnormal calcium homeostasis, or a disease or incompetence induced by reduced CaSR function and include specifically diarrhea, diseases associated with acid secretion in the alimentary tract, eating disorders such as bulimia, hyperparathyroidism (primary and secondary hyperparathyroidism, secondary hyperparathyroidism in maintenance dialysis), etc.

As used herein, diarrhea includes all types of diarrheas including irritable bowel syndrome, functional diarrhea, inflammatory bowel disorder, diverticulitis, bacterial diarrhea, dyspepsia, etc.

The diseases associated with acid secretion in the alimentary tract include ulcer and inflammatory disorders in the digestive tract such as stomach, small intestine (duodenum, jejunum and ileum) and also include exogenous diseases induced by drugs (non-steroidal inflammatory drugs, alcohol, etc.).

The term "peptic ulcer" includes gastric ulcer, duodenal ulcer, gastritis, NSAIDs-induced enteritis, reflux esophagitis, non-erosive gastroesophageal reflux disease, etc. The compound, pharmaceutical composition, CaSR agonist agent, preventive or therapeutic agent for diarrhea, preventive or therapeutic agent for hyperparathyroidism or preventive or therapeutic agent for peptic ulcer, of the present invention may contain all glutamate derivatives embraced by the glutamate derivative of the present invention represented by general formula (I) or pharmaceutically acceptable salts, alone or in combination of 2 or 3 more, and may further contain all solid or liquid carrier or additives that are pharmaceutically, physiologically or experimentally acceptable or acceptable for food handling.

The method of applying the compound of the present invention as the pharmaceutical composition, CaSR agonist agent, preventive or therapeutic agent for diarrhea, preventive or therapeutic agent for hyperparathyroidism or preventive or therapeutic agent for peptic ulcer is not particularly limited, and any invasive or non-invasive administration such as oral administration and injection is applicable. Suppository or percutaneous administration is also applicable. The active ingredient may be formulated and administered in the form of a conventional pharmaceutical composition together with a solid or liquid pharmaceutical carrier suitable for oral administration, injection, etc. The pharmaceutical composition includes, for example, a solid preparation such as a tablet, granule, powder, capsule, etc., a liquid preparation such as a solution, suspension, emulsion, etc., and a lyophilizate preparation, and the like. These preparations can be prepared in a conventional manner in pharmaceutical preparations. In addition, the pharmaceutical composition of the present invention may further contain any pharmaceutically or pharmacologically acceptable, solid or liquid carriers, additives and the like.

Examples of the carrier described above are glucose, lactose, sucrose, starch, mannitol, dextrin, glycerides of fatty acids, polyethylene glycols, hydroxyethyl starch, ethylene glycols, polyoxyethylene sorbitan fatty acid esters, gelatin, albumin, amino acids, water and a physiological saline solution. If necessary, conventional additives such as stabilizers, moisturizers, emulsifiers, binders, tonicity agents, etc. can be appropriately added to the CaSR agonist agent of the present invention.

The above additives are not particularly limited as long as they are ordinarily used purposes depending upon purposes to meet the purposes. Examples of the additives include flavoring agents, sugars, sweetening agents, dietary fibers, vitamins, amino acids such as a monosodium glutamate (MSG), etc., nucleic acids such as an inosine monophosphate (IMP), etc., inorganic salts such as sodium chloride, water, and the like.

The CaSR agonist agent of the present invention can be used in any form such as dry powder, paste, a solution, etc., irrespective of physical properties. The CaSR agonist agent of the present invention can also be used in medical drugs, quasi drugs, food products, reagents, or the like.

The CaSR agonist agent, preventive or therapeutic agent for diarrhea, preventive or therapeutic agent for hyperparathyroidism and preventive or therapeutic agent for peptic ulcer, of the present invention can be used as foods and beverages or supplements wherein each agent has each effect. These agents can be prepared into foods and beverages indicating on the container or package thereof that there are the therapeutic or preventive effects on, e.g., diarrhea. The form of the foods and beverages is not particularly limited, and the foods and beverages can be produced by the same manner as in conventional food products, using the same materials as used in producing conventional food products, except that the compound having CaSR agonist activity is dispensed. Examples of food products include seasonings; beverages such as juice and milk; confectionery; jellies; health foods; processed agricultural products; processed animal products such as milk and cheese; food supplements, and the like.

The amount of the compound, pharmaceutical composition, CaSR agonist agent, preventive or therapeutic agent for diarrhea, preventive or therapeutic agent for hyperparathyroidism or preventive or therapeutic agent for peptic ulcer, of the present invention can be appropriately adjusted depending upon each purpose. For example, in the case that they are orally administered to a target subject, a total amount of the glutamate derivative represented by general formula (I) or pharmaceutically acceptable salts thereof is preferably 0.01 mg to 10 g per 1 kg of body weight in single administration, and more preferably 0.1 mg to 1 g.

The frequency of administration is not particularly limited, and the composition can be administered once or several times per day.

Where the compound, pharmaceutical composition, CaSR agonist agent, preventive or therapeutic agent for diarrhea, preventive or therapeutic agent for hyperparathyroidism or preventive or therapeutic agent for peptic ulcer, of the present invention is used in food products or reagents, it is preferred to use 0.001 mg to 10 g per one prescription, and more preferably, 0.01 mg to 1 g per one prescription.

The amount of the glutamate derivative of the present invention represented by general formula (I) or pharmaceutically acceptable salts thereof contained in the compound, pharmaceutical composition, CaSR agonist agent, preventive or therapeutic agent for diarrhea, preventive or therapeutic agent for hyperparathyroidism or preventive or therapeutic agent for peptic ulcer, of the present invention is not particularly limited so long as the amount meets the use range described above, and is preferably 0.000001 to 99.9999% by weight, more preferably 0.00001 to 99.999% by weight, and particularly preferably 0.0001 to 99.99% by weight, based on the dry weight.

The compound, pharmaceutical composition, CaSR agonist agent, preventive or therapeutic agent for diarrhea, preventive or therapeutic agent for hyperparathyroidism or preventive or therapeutic agent for peptic ulcer, of the present invention may further contain one or more known substances having the CaSR agonist activity.

Examples of the known substances having the CaSR agonist activity include cations such as calcium, gadolinium, etc.; basic peptides such as polyarginine, polylysine, etc.; polyamines such as putrescine, spermine, spermidine, etc.; proteins such as protamine, etc.; amino acids such as phenylalanine, etc.; peptides such as glutathione, etc.; and analogues of cinacalcet, but they are not limited thereto.

In addition to the known substances having the CaSR agonist activity, the compound, pharmaceutical composition, CaSR agonist agent, preventive or therapeutic agent for diarrhea, preventive or therapeutic agent for hyperparathyroidism or preventive or therapeutic agent for peptic ulcer, of the present invention may also contain any known substance depending upon purposes.

The compound of the present invention has the CaSR agonist activity and can be used as a kokumi-imparting activity. As used herein, the term "kokumi" taste is intended to mean the taste that cannot be expressed with five basic tastes of sweetness, saltiness, sourness, bitterness and umami, and means the taste of not only the basic tastes but also the taste that further enhances marginal tastes of the basic tastes, such as thickness, growth (mouthfulness), continuity, and harmony. The term "kokumi-imparting agent" is intended to mean an agent or substance that can enhance at least one of the five basic tastes of sweetness, saltiness, sourness, bitterness and umami, and impart the marginal tastes of the basic tastes such as thickness, growth (mouthfulness), continuity, and harmony. On the other hand, the compound of the present invention can also be used as a sweetness enhancer, a salty taste enhancer, a sour taste enhancer, a bitter taste enhancer or an umami taste enhancer, accompanied by improvement of the quality of taste.

The kokumi-imparting effect can be confirmed by the method such as a gustatory test by human volunteers as described in EXAMPLES of the present invention, but not limited thereto.

The kokumi-imparting agent of the present invention may comprise any glutamate derivative of the present invention represented by general formula (I) or pharmaceutically acceptable salts thereof, alone or in combination of optional two or more thereof. Furthermore, various other additives or the like may also be added to the kokumi-imparting agent.

Additives are not particularly limited and can be used as the additive described above so long they are known to be used as additives to foods and beverages such as seasonings, food products, beverages, etc. Examples of the additives include flavoring agents, sugars, sweetening agents, dietary fibers, vitamins, amino acids such as a monosodium glutamate (MSG), etc., nucleic acids such as an inosine monophosphate (IMP), etc., inorganic salts such as sodium chloride, etc., water, and the like.

The present invention also provides foods and beverages comprising the glutamate derivative of the present invention represented by general formula (I) above. The amount of the glutamate derivative of the present invention represented by general formula (I) above or pharmaceutically acceptable salts thereof or the kokumi-imparting agent used in foods and beverages can be the amount effective for imparting the kokumi taste and is appropriate adjusted depending on use. For example, when used in seasonings, food products or beverages, a total amount of the glutamate derivative of the present invention represented by general formula (I) or pharmaceutically acceptable salts thereof or the kokumi-imparting agent is 1 ppb to 99.9% by weight in seasonings, food products or beverages, and preferably 10 ppb to 99.9% by weight.

Accordingly, kokumi-imparted foods or beverages can be produced by adding one or more of the glutamate derivatives of the present invention represented by general formula (I) above or pharmaceutically acceptable salts thereof or the kokumi-imparting agents to foods or beverages in 1 ppb to 99.9% by weight, and preferably 10 ppb to 99.9% by weight.

Furthermore, the kokumi-imparted foods or beverages can also be produced by adding the kokumi-imparted seasonings containing one or more of the glutamate derivatives of the present invention represented by general formula (I) above or pharmaceutically acceptable salts thereof or the kokumi-imparting agents to foods or beverages in an amount of 0.01 to 10% by weight, and preferably 0.1 to 10% by weight based on the foods or beverages.

The kokumi-imparting agent of the present invention may further contain one or more kinds of a known substance(s) having the CaSR agonist activity.

The known substance above having the CaSR agonist activity include, for example, cations such as calcium, gadolinium, etc.; basic peptides such as polyarginine, polylysine, etc.; polyamines such as putrescine, spermine, spermidine, etc.; proteins such as protamine, etc.; amino acids such as phenylalanine, etc.; peptides such as glutathione, etc.; analogues of cinacalcet, etc., but are not limited thereto.

Furthermore, in addition to the known substance having the CaSR agonist activity, the kokumi-imparting agent of the present invention may also contain any known substance depending on purposes.

When the glutamate derivative of the present invention represented by general formula (I) above or pharmaceutically acceptable salts thereof or the kokumi-imparting agent is added to foods and beverages, the form is not limited in terms of physical properties such as dry powder, paste, a solution, etc.

(Representative Process of Synthesizing the Glutamate Derivative Represented by General Formula (I))

The representative processes of producing the compound of the present invention are illustrated below.

In the following production processes, it is sometimes effective in terms of processing technology to previously replace a functional group with an appropriate protective group, i.e. a group capable of easily converting into the functional group at the stage of a starting material or its intermediate, if it is preferable for the functional group. Then, the protective group is removed, if necessary, to obtain the intended compound. Such functional groups include, for example, an amino group, a hydroxyl group, a carboxyl group, etc. Examples of the protective groups for these functional groups include t-butoxycarbonyl (Boc), benzyloxycarbonyl (Z or Cbz), 9-fluorenylmethoxycarbonyl (Fmoc), etc. as a protective group for the amino group; t-butyl (tBu), benzyl (Bn or Bzl), etc. as a protective group for the carboxyl group; and protective groups described in Protective Groups in Organic Synthesis, third edition (T. W. Green and P. G. M. Wuts, JOHN WILEY & SONS, INC.). These protective groups may be appropriately used depending upon reaction conditions. The introduction and deprotection of these protective groups can be conducted at the right time in accordance with the procedures described in the reference book described above. For example, functional groups represented by Prot1 and Prot2 in the following processes 1 and 2 indicate that they are used as protective groups, but functional group is not limited thereto.

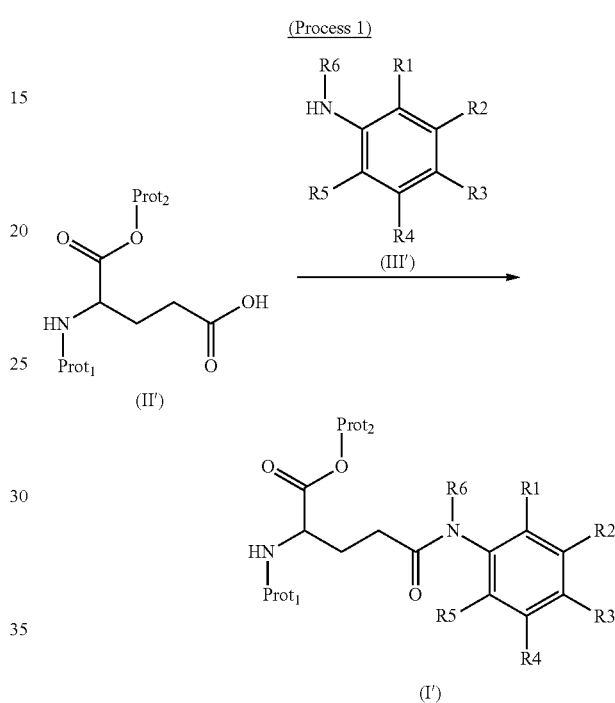

Process 1 is a reaction for producing compound (I') by condensation between a carboxylic acid and an amine using compound (II') and compound (III').

The reaction can be carried out in a conventional manner using the equivalent of the compound (II') and the amine derivative (III') or an excess of either one in the presence of a condensing agent. Examples of the condensing agent which are advantageously used include N,N-dicyclohexylcarbodiimide (DCC), 1-ethyl-3-[3-(N,N-dimethylamino)propyl]carbodiimide (EDCI or WSC), O-benzotriazol-1-yl-N,N,N',N'-tetramethyluronium hexafluorophosphate (HBTU), carbonyldiimidazole (CDI), 4-(4,6-dimethoxy-1,3,5-triazin-2-yl)-4-methylmorpholinium chloride (DMTMM), 2-(7-azabenzotriazol-1-yl)-N,N,N',N'-tetramethyluronium hexafluorophosphate (HATU), etc. These condensing agents are used in an equivalent or excess amount based on the carboxylic acid. A solvent that is inert to the reaction, e.g., N,N-dimethylformamide (DMF), dioxane, water, methanol, ethanol, tetrahydrofuran (THF), dichloromethane, dichloroethane, diethyl ether, chloroform, dimethoxyethane (DME), ethyl acetate, toluene, acetonitrile, dimethylsulfoxide (DMSO), a solvent mixture thereof, etc., may be used as a solvent. Preferably, solvents are appropriately chosen depending on a raw material, kind of a condensing agent, and the like. The reaction can proceed smoothly in the presence of a base such as triethylamine, diisopropylethylamine, N-methylmorpholine, pyridine, 4-dimethylaminopyridine, etc.; or by reacting these bases as a solvent. Though the reaction is usually performed while cooling to at room temperature, it is sometimes preferred to conduct the reaction under heating depending on the conditions of the condensation reaction.

The compound (I') can also be produced by a process of introducing the carboxylic acid into its active derivative and then condensing the derivative with the amine. In this case, the compound (II') and the amine derivative (III') are used in an equivalent amount or in an excess amount of either one. Examples of the active derivative of the carboxylic acid include a phenol compound such as p-nitrophenol, etc.; an activated ester obtained by reacting a N-hydroxyamine compound such as 1-hydroxysuccinimide (HOSu), 1-hydroxybenzotriazole (HOBt) and 7-aza-1-hydroxybenzotriazole (HOAt); a mixed acid anhydride obtained by reacting a monoalkyl carbonate and an organic acid; a phosphoric mixed acid anhydride obtained by reacting diphenylphosphoryl chloride and N-methylmorpholine; an acid azide obtained by sequentially reacting an ester with a hydrazine and an alkyl nitrite; an acid halide such as an acid chloride, an acid fluoride, etc.; and a symmetrical acid anhydride, and the like.

Where the active derivative of the carboxylic acid is synthesized, an activating reagent is used in an equivalent or excess amount based on the compound (II'). Any reaction can be used even under reaction conditions other than those in the case above, so long as it is a reaction that forms an amide bond.

The glutamate derivative of the present invention represented by general formula (I) can be produced by a reaction for selectively removing $Prot_1$ from, e.g., the compound (I') protected. Alternatively, a process which comprises deprotecting $Prot_1$ and $Prot_2$ and then esterifying, e.g., in an alcohol solvent such as methanol in the presence of an acid catalyst such as hydrogen chloride, or a process which comprises selectively removing $Prot_2$ alone, reacting with an alcohol in the presence of a condensing agent for esterification as in the process above and then removing $Prot_1$, if necessary.

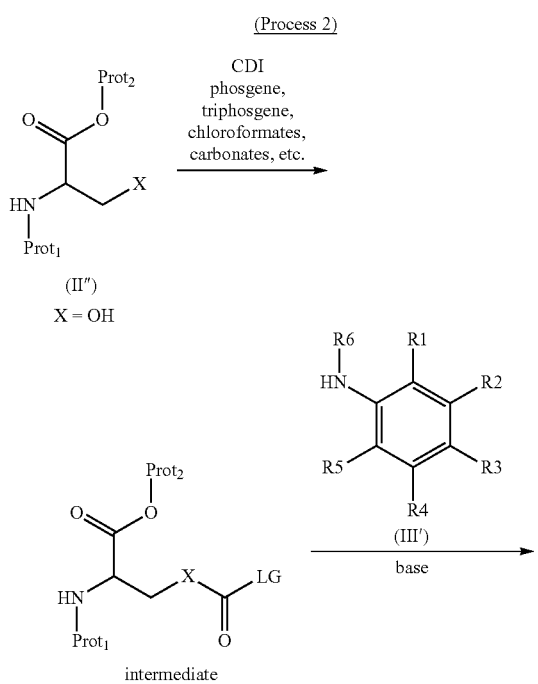

(Process 2)

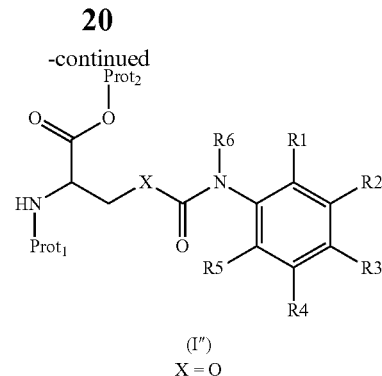

(I'')
X = O

This process involves a reaction which comprises obtaining the intermediate from the compound (II'') and then reacting the resulting intermediate with the compound (III') to produce the compound (I'').

According to the reaction, the intermediate can be obtained by reacting the compound (II'') with an equivalent or a little excess amount of a reagent such as N,N-carbonyldiimidazole, phosgene, triphosgene, benzyl chloroformate, methyl carbonate, etc. In this case, the reaction is carried out preferably in a solvent inert to the reaction, e.g., N,N-dimethylformamide (DMF), dioxane, tetrahydrofuran (THF), dichloromethane, dichloroethane, diethyl ether, chloroform, dimethoxyethane (DME), ethyl acetate, toluene, acetonitrile, dimethylsulfoxide (DMSO), or a solvent mixture thereof, or the like. Though the reaction is usually conducted while cooling to at room temperature, it is sometime preferred to perform the reaction with heating depending on the reagent and compound. The resulting intermediate is transferred to a preferable solvent, if necessary, and the reaction is carried out using the intermediate and the compound (III') in an equivalent or a little excessive amount of either one. The reaction can also be performed in the presence of an organic base such as triethylamine or an inorganic base such as potassium carbonate, etc. Though the reaction is usually conducted with cooling to heating at about 100° C., it is sometimes necessary to conduct the reaction with further heating, depending on the compound. In addition to the process above, any reaction can be used so long as it is a reaction of forming the carbamate.

The glutamate derivative of the present invention represented by general formula (I) can be produced by a reaction of selectively removing $Pro_1$ from, e.g., the compound (I'') protected. Alternatively, a process which comprises deprotecting $Prot_1$ and $Prot_2$ and then esterifying, e.g., in an alcohol solvent such as methanol in the presence of an acid catalyst such as hydrogen chloride, or a process which comprises selectively removing $Prot_2$ alone, reacting with an alcohol in the presence of a condensing agent for esterification as in the process above and then removing $Prot_1$, if necessary.

(Process 3)

The compound of the present invention thus produced can be used as it is in a free form or its salt, or can be isolated or purified by conventional chemical procedures in the art, for example, extraction, precipitation, fractional chromatography, fractional crystallization, recrystallization, etc. The salts of the compound can be produced by applying a conventional salt-forming reaction to the free form of the compound of the present invention.

Where the compound of the present invention has asymmetric carbons, its optical isomers exist. The optical isomers can be produced by the procedures of converting the compound into a diastereomeric salt with an optically active acid or base followed by fractional crystallization, optical resolution in a conventional manner such as column chromatography, etc., synthesis using an optically active raw compound, or the like.

In formula (I), configuration of the carbon atom to which E-CO— and the amino group bind is preferably S-configuration.

EXAMPLES

Hereinafter, the present invention will be described in more detail with reference to EXAMPLES, but is not deemed to be limited thereto.

As used herein, the conventional manner is intended to mean the procedures generally used as chemical operations represented by liquid separation, drying, filtration and concentration.

As used herein, the purification step A is intended to mean the procedures which comprises applying a crude product obtained in a conventional manner to a reversed phase high-performance liquid chromatography using octadecylsilyl silica gel (ODS) as a filler, followed by elution with a solution mixture of water and acetonitrile containing 0.1% (v/v) trifluoroacetic acid, concentrating and freeze-drying the fraction of interest.

Hereinafter, synthesis of the representative compounds of the present invention listed in TABLE 1 is described in more detail, by referring to EXAMPLES but the compound of the present invention is not deemed to be limited to these EXAMPLES.

The structures of the compounds synthesized by the following processes are shown in TABLE 1, together with MS values or NMR measurement data.

Example I

Synthesis Examples

Example 1

Synthesis of 3-[(4S)-4-amino-5-methoxy-5-oxopentanamide]benzene-1-sulfonic acid

Boc-Glu-OMe, 130 mg (0.5 mmol), 190 mg (0.5 mmol) of 2-(7-azabenzotriazol-1-yl)-N,N,N',N'-tetramethyluronium hexafluorophosphate (HATU), 70 mg (0.5 mmol) of 7-aza-1-hydroxybenzotriazole (HOAt) and 87 mg (0.5 mmol) of 3-aminobenzenesulfonic acid were suspended in 2.0 ml of methylene chloride, and 0.5 ml of triethylamine was added to the suspension. The mixture was stirred at room temperature overnight. After the solvent was removed by distillation, the mixture was purified in accordance with the purification step A to give the intermediate. The intermediate was dissolved in 4.0 ml of trifluoroacetic acid (TFA) and stirred at room temperature for an hour. After the solvent was removed by distillation, the mixture was purified in accordance with the purification step A to give 7.4 mg of the title compound.

Yield amount: 7.4 mg

Example 2

Synthesis of 3-[(4S)-4-amino-5-methoxy-5-oxopentanamide]-5-chloro-2-hydroxybenzene-1-sulfonic acid The title compound was obtained in the same way except that 3-amino-5-chloro-2-hydroxybenzenesulfonic acid was replaced for 3-aminobenzenesulfonic acid used in EXAMPLE 1.

Yield amount: 17.4 mg

Example 3

Synthesis of 3-[(4S)-4-amino-5-methoxy-5-oxopentanamide]-5-chloro-4-methylbenzene-1-sulfonic acid The title compound was obtained in the same way except that 3-amino-5-chloro-4-methylbenzenesulfonic acid was replaced for 3-aminobenzenesulfonic acid used in EXAMPLE 1.

Yield amount: 5.1 mg

Example 4

Synthesis of 3-[(4S)-4-amino-5-(benzyloxy)-5-oxopentanamide]-5-chloro-2-hydroxybenzene-1-sulfonic acid The title compound was obtained in the same way except that Boc-Glu-OBzl and 3-amino-5-chloro-2-hydroxybenzenesulfonic acid were replaced for Boc-Glu-OtBu and 3-sulfoaniline, respectively, used in REFERENCE SYNTHESIS EXAMPLE 1.

Example 5

Synthesis of 3-({[(2S)-2-amino-3-methoxy-3-oxopropoxy]carbonyl}amino)benzene-1-sulfonic acid Boc-Ser-OMe, 110 mg (0.5 mmol), and 87 mg (0.5 mmol) of 3-aminobenzenesulfonic acid were dissolved in 1 ml of pyridine, and 50 mg of triphosgene was added to the solution. The mixture was stirred at room temperature for 2 hours and the solvent was then distilled off. The resulting residue was purified according to the purification step A to give the crude product of the protected title compound. The crude product obtained was dissolved in 1 ml of methylene chloride and 1 ml of trifluoroacetic acid. The solution was stirred for 30 minutes at room temperature. After the solvent was distilled off, the mixture was purified in accordance with the purification step A to give the title compound.

Yield amount: 20.17 mg

Example 6

Synthesis of 5-({[(2S)-2-amino-3-methoxy-3-oxopropoxy]carbonyl}amino)-3-chloro-2-methylbenzene-1-sulfonic acid The title compound was obtained in the same way except that 5-amino-3-chloro-2-methylbenzenesulfonic acid was replaced for 3-aminobenzenesulfonic acid used in EXAMPLE 5.

Yield amount: 81.76 mg

Example 7

Synthesis of 3-[(4S)-4-amino-5-ethoxy-5-oxopentanamide]-5-chloro-2-hydroxybenzene-1-sulfonic acid

Synthesis of Boc-Glu-OEt

Boc-Glu (OBzl)-OH, 1.01 g (3.0 mmol), 620 mg (3.1 mmol) of N,N-dicyclohexylcarbodiimide (DCC) and 475 mg (3.1 mmol) of 1-hydroxybenzotriazole monohydrate (HOBt.H$_2$O) were suspended in 12 ml of methylene chloride. The suspension was cooled to 0° C. and 175 μl of ethyl alcohol was added thereto. After reverting to room temperature, stirring was continued overnight. The mixture was extracted with ethyl acetate/water. After the organic layer was washed with aqueous saturated sodium chloride solution (brine), sodium sulfate was added thereto and dried. The organic layer was concentrated under reduced pressure. The resulting residue was dissolved in 12 ml of methanol, and 100 mg of 10% Pd/C was added to the solution. The mixture was stirred in a hydrogen atmosphere overnight and purified in accordance with the purification step A to give the crude product of the title compound.

ESI (m/Z): 276 [M+H]+

Step 2

Synthesis of 3-[(4S)-4-amino-5-ethoxy-5-oxopentanamide]-5-chloro-2-hydroxybenzene-1-sulfonic acid After 92 mg (0.33 mmol) of the compound obtained in Step 1, 130 mg (0.33 mmol) of HATU, 45 mg (0.33 mmol) of HOAt and 77 mg (0.33 mmol) of 3-amino-5-chloro2-hydroxybenzenesulfonic acid were suspended in 1.0 ml of DMF, 0.25 ml of pyridine was added to the suspension. The mixture was stirred at room temperature overnight. The solvent was removed by distillation and the mixture was purified in accordance with the purification step A to give the intermediate. The intermediate was dissolved in 4.0 ml of TFA, followed by stirring at room temperature for an hour. The solvent was removed by distillation and the mixture was purified in accordance with the purification step A to give 47.2 mg of the title compound.

Yield amount: 47.2 mg

Example 8

Synthesis of 3-[(4S)-4-amino-5-oxo-5-(propan-2-yloxy)pentanamide]-5-chloro-2-hydroxybenzene-1-sulfonic acid The title compound was obtained in the same way except that 2-propanol was replaced for ethyl alcohol used in EXAMPLE 7.

Yield amount: 42.6 mg

TABLE 1

| Ex. No. | Structure | 1H-NMR | MS(ESI, m/z) |
|---|---|---|---|
| 1 | (structure) | 1H-NMR (DMSO-d6, 400 MHz): δ 10.1 (s, 1H), 8.39 (s, 3H), 7.83 (s, 1H), 7.59-7.58 (m, 1H), 7.38-7.21 (m, 2H), 4.12-4.11 (m, 1H), 3.75 (s, 3H), 2.46-2.44 (m, 2H), 2.12-2.08 (m, 2H) | 317 [M + H]+ |
| 2 | (structure) | 1H-NMR (DMSO-d6, 400 MHz) δ: 11.1 (s, 1H), 9.39 (s, 1H), 8.35 (s, 3H), 8.03 (s, 1H), 7.14 (s, 1H), 4.11-4.09 (m, 1H), 3.75 (s, 3H) 2.65-2.59 (m, 2H), 2.12-2.04 (m, 2H) | 367, 369 [M + H]+ |
| 3 | (structure) | 1H-NMR (DMSO-d6, 400 MHz) δ: 9.69 (s, 1H), 8.38 (s, 3H), 7.52 (s, 1H), 7.41 (s, 1H) 4.13-4.12 (m, 1H), 3.77 (s, 3H) 2.57-2.54 (m, 2H) , 2.19 (s, 3H) , 2.11-2.10 (m, 2H) | 365, 367 [M + H]+ |
| 4 | (structure) | | 443 [M + H]+ |

TABLE 1-continued

| Ex. No. | Structure | 1H-NMR | MS(ESI, m/z) |
|---|---|---|---|
| 5 | (structure) | 1H-NMR (D2O, 400 MHz) δ: 7.73(s, 1H), 7.46 (m, 3H), 4.66 (dd, 1H), 4.58 (dd, 1H), 4.50 (dd, 1H), 3.82 (s, 3H) | 319 [M + H]+ |
| 6 | (structure) | 1H-NMR(D2O, 400 MHz)δ: 7.40-7.72(m, 2H), 4.47-4.67(m, 3H), 3.82(s, 3H), 2.52(s, 3H) | 367, 369 [M + H]+ |
| 7 | (structure) | 1H-NMR (DMSO-d6, 400 MHz)δ: 11.1 (s, 1H), 9.39 (s, H), 8.31 (s, 3H), 8.03 (s, 1H), 7.14 (s, 1H), 4.24-4.18 (m, 2H), 4.09-4.06 (m, 1H), 2.67-2.59 (m, 2H), 2.12-2.04 (m, 2H), 1.26-1.23 (m, 3H) | 381, 383 [M + H]+ |
| 8 | (structure) | 1H-NMR (DMSO-d6, 400 MHz) δ: 11.0 (s, 1H), 9.34(s, 1H), 8.24(s, 3H), 7.96(s, 1H), 7.07(s, 1H), 4.97-4.91 (m, 1H), 3.98-3.97(m, 1H) 2.57-2.52 (m, 2H), 2.03-1.96(m, 2H), 1.20-1.18 (m, 6H) | 395, 397 [M + H]+ |

Synthesis of the reference compounds listed in TABLE 2 below will be described in more details, by referring to REFERENCE SYNTHESIS EXAMPLES. The compound of the present invention also includes, but not limited thereto, the compounds described in REFERENCE SYNTHESIS EXAMPLES 1 to 18 in which the carboxyl group in the amino acid moiety is substituted with the E-CO— group.

TABLE 2

(I-F)

| Ref Cpd. No. | R¹ | R² | R³ | R⁴ | R⁵ | R⁶ | X |
|---|---|---|---|---|---|---|---|
| 1 | H | SO$_3$H | H | H | H | H | CH$_2$ |
| 2 | H | SO$_3$H | OMe | H | H | H | CH$_2$ |
| 3 | H | SO$_3$H | H | H | OMe | H | CH$_2$ |
| 4 | H | SO$_3$H | Me | H | Me | H | CH$_2$ |
| 5 | H | SO$_3$H | Me | H | H | H | CH$_2$ |
| 6 | H | SO$_3$H | H | NO$_2$ | OH | H | CH$_2$ |
| 7 | OH | SO$_3$H | H | Cl | H | H | CH$_2$ |
| 8 | H | SO$_3$H | H | H | OH | H | CH$_2$ |
| 9 | H | SO$_3$H | Cl | H | H | H | CH$_2$ |
| 10 | OH | SO$_3$H | H | H | H | H | CH$_2$ |
| 11 | H | SO$_3$H | OH | H | H | H | CH$_2$ |
| 12 | H | SO$_3$H | H | H | H | CH$_3$ | CH$_2$ |
| 13 | H | SO$_3$H | H | H | H | H | O |
| 14 | H | CO$_2$H | H | H | H | H | CH$_2$ |
| 15 | OH | CO$_2$H | H | H | H | H | CH$_2$ |
| 16 | H | CO$_2$H | H | Br | H | H | CH$_2$ |
| 17 | H | PO(OMe)OH | H | H | H | H | CH$_2$ |
| 18 | H | PO(OH)$_2$ | H | H | H | H | CH$_2$ |
| 19 | H | NO$_2$ | H | H | H | H | CH$_2$ |
| 20 | H | H | H | H | H | H | CH$_2$ |

Reference Example I

Reference Synthesis Example 1

Synthesis of N$^5$-(3-sulfophenyl)-L-glutamine (Reference Compound No. 1)

Boc-Glu-OtBu (75 mg, 0.247 mmol), HATU (112 mg, 0.296 mmol) and HOAt (41 mg, 0.296 mmol) were dissolved in 1 ml of DMF, and triethylamine (52 μl) was added to the solution. The mixture was stirred at room temperature for 10 minutes. 3-Sulfoaniline (43 mg, 0.247 mmol) was added to the mixture, followed by stirring at room temperature overnight. After the solvent was removed by distillation, the mixture was purified according to the purification step A. The resulting intermediate was dissolved in 2 ml of trifluoroacetic acid. After stirring for 3 hours at room temperature, the solvent was distilled off. The product was purified using the purification step A to give the title compound.

Yield amount: 30.8 mg (0.10 mmol), yield: 41%

1H-NMR (D$_2$O, 300 MHz): δ 7.89 (s, 1H), 7.67-7.62 (m, 2H), 7.58-7.53 (m, 1H), 3.99 (t, 1H, J=6.4 Hz), 2.73-2.66 (m, 2H), 2.33-2.25 (m, 2H)

ESI (m/z): 303 [M+H]+, 301 [M−H]−

Reference Synthesis Example 2

Synthesis of N$^5$-(4-methoxy-3-sulfophenyl)-L-glutamine (Reference Compound No. 2)

The title compound was obtained in the same way except that p-anisidine-3-sulfonic acid was used in place of 3-sulfoaniline of REFERENCE SYNTHESIS EXAMPLE 1.

Yield amount: 24.7 mg, yield: 23%

1H-NMR (D$_2$O, 300 MHz): δ 7.96 (s, 1H), 7.53 (d, 1H), 7.04 (d, 1H), 3.98 (t, 1H), 3.78 (s, 3H), 2.63-2.52 (m, 2H), 2.30-2.05 (m, 2H)

ESI (m/z): 333 [M+H]+

Reference Synthesis Example 3

Synthesis of N$^5$-(2-methoxy-5-sulfophenyl)-L-glutamine (Reference Compound No. 3)

The title compound was obtained in the same way except that o-anisidine-5-sulfonic acid was used in place of 3-sulfoaniline of REFERENCE SYNTHESIS EXAMPLE 1.

Yield amount: 75.7 mg, yield: 69%

1H-NMR (D$_2$O, 300 MHz): δ 7.65 (s, 1H), 7.45 (d, 1H), 7.04 (d, 1H), 3.96 (t, 1H), 3.79 (s, 3H), 2.80-2.50 (m, 2H), 2.25-2.10 (m, 2H)

ESI (m/z): 333 [M+H]+

Reference Synthesis Example 4

Synthesis of N$^5$-(2,4-dimethyl-5-sulfophenyl)-L-glutamine (Reference Compound No. 4)

The title compound was obtained in the same way except that sodium 2,4-dimethylaniline-5-sulfonate was used in place of 3-sulfoaniline of REFERENCE SYNTHESIS EXAMPLE 1.

Yield amount: 70.3 mg, yield: 64%

1H-NMR (D$_2$O, 300 MHz): δ 7.55 (s, 1H), 7.17 (s, 1H), 3.97 (t, 1H), 2.67-2.55 (m, 2H), 2.43 (s, 3H), 2.30-2.15 (m, 2H), 2.08 (s, 3H)

ESI (m/z): 331 [M+H]+

Reference Synthesis Example 5

Synthesis of N$^5$-(4-methyl-3-sulfophenyl)-L-glutamine (Reference Compound No. 5)

The title compound was obtained in the same way except that 5-amino-2-methylbenzene-1-sulfonic acid was used in place of 3-sulfoaniline of REFERENCE SYNTHESIS EXAMPLE 1.

Yield amount: 79.3 mg, yield: 76%

1H-NMR (D$_2$O, 300 MHz): δ 7.76 (s, 1H), 7.34 (d, 1H), 7.24 (d, 1H), 3.93 (t, 1H), 2.60-2.45 (m, 2H), 2.44 (s, 3H), 2.30-2.00 (m, 2H)

ESI (m/z): 317 [M+H]+

Reference Synthesis Example 6

Synthesis of N$^5$-(2-hydroxy-3-nitro-5-sulfophenyl)-L-glutamine (Reference Compound No. 6)

The title compound was obtained in the same way except that 3-amino-4-hydroxy-5-nitrobenzenesulfonic acid was used in place of 3-sulfoaniline of REFERENCE SYNTHESIS EXAMPLE 1.

Yield amount: 73.8 mg, yield: 62%

1H-NMR (D$_2$O, 300 MHz): δ 8.37 (s, 1H), 8.24 (s, 1H), 3.94 (t, 1H), 2.64-2.70 (m, 2H), 2.09-2.23 (m, 2H)
ESI (m/z): 364 [M+H]+

Reference Synthesis Example 7

Synthesis of N$^5$-(5-chloro-2-hydroxy-3-sulfophenyl)-L-glutamine (Reference Compound No. 7)

Boc-Glu-OtBu (100 mg, 0.33 mmol) and HOBt monohydrate (65.6 mg, 0.43 mmol) were dissolved in 2 ml of DMF, and triethylamine (0.137 ml) was added to the solution. After cooling to 0° C., diisopropylcarbodiimide (66.4 µl, 0.43 mmol) and 2-amino-4-chlorophenol-6-sulfonic acid (73.7 mg, 0.33 mmol) were added, followed by stirring at room temperature overnight. After the solvent was removed by distillation, the mixture was purified according to the purification step A. The resulting intermediate was dissolved in 2 ml of TFA. The solution was stirred at room temperature for 2 hours, and 2 ml of methylene chloride was added thereto. The precipitate was taken out by filtration to give the title compound.
Yield amount: 16.8 mg, yield: 14.4%
1H-NMR (DMSO-d6, 300 MHz): δ 11.07 (s, 1H), 9.39 (s, 1H), 8.20-8.40 (br, 2H), 8.02 (s, 1H), 7.14 (s, 1H), 3.95 (t, 1H, J=6.4 Hz), 2.64 (m, 2H), 2.07 (m, 2H)
ESI (m/z): 353 [M+H]+

Reference Synthesis Example 8

Synthesis of N$^5$-(2-hydroxy-5-sulfophenyl)-L-glutamine (Reference Compound No. 8)

The title compound was obtained in the same way except that 2-aminophenol-4-sulfonic acid was used in place of 2-amino-4-chlorophenol-6-sulfonic acid of REFERENCE SYNTHESIS EXAMPLE 7.
Yield amount: 31.5 mg, yield: 30%
1H-NMR (D$_2$O, 300 MHz): δ 7.77 (s, 1H), 7.44 (d, 1H), 6.94 (d, 1H), 4.00-3.85 (m, 1H), 2.65-2.57 (m, 2H), 2.19-2.10 (m, 2H)
ESI (m/z): 319 [M+H]+

Reference Synthesis Example 9

Synthesis of N$^5$-(4-chloro-3-sulfophenyl)-L-glutamine (Reference Compound No. 9)

The title compound was obtained in the same way except that 4-chloroaniline-3-sulfonic acid (68.4 mg) was used in place of 2-amino-4-chlorophenol-6-sulfonic acid of REFERENCE SYNTHESIS EXAMPLE 7.
Yield amount: 47.8 mg, yield: 43%
1H-NMR (D$_2$O, 300 MHz): δ 7.91 (s, 1H), 7.50-7.45 (m, 2H), 4.00-3.85 (m, 1H), 2.60-2.40 (m, 1H), 2.25-2.15 (m, 2H)
ESI (m/z): 337 [M+H]+

Reference Synthesis Example 10

Synthesis of N$^5$-(2-hydroxy-3-sulfophenyl)-L-glutamine (Reference Compound No. 10)

Z-Glu-OBn (371 mg, 1 mmol) was dissolved in methylene chloride (1 ml), and CDI (180 mg, 1.1 mmol) was added to the solution. The mixture was stirred at room temperature for 30 minutes. 2-Amino-4-chlorophenol-6-sulfonic acid (223 mg, 1 mmol) and THF (1 ml) were added to the mixture. The mixture was then stirred overnight at room temperature. After the solvent was removed by distillation, the mixture was purified in accordance with the purification step A. The resulting intermediate was dissolved in a methanol-water solvent mixture. A catalytic amount of Pd/C was added to the solution. The mixture was stirred overnight at room temperature in a hydrogen atmosphere. After the catalyst was filtered off, the solvent was removed by distillation. The mixture was purified according to the purification step A to give the title compound.
Yield amount: 120 mg (0.40 mmol), yield: 40%
1H-NMR (D$_2$O, 300 MHz): δ 7.67 (d, 1H, J=7.9 Hz), 7.62 (d, 1H, J=8.2 Hz), 7.07 (dd, 1H, J=7.9 Hz, 8.2 Hz), 3.92-3.97 (m, 1H), 2.59-2.64 (m, 2H), 2.25-2.20 (m, 2H)
ESI (m/z): 319 [M+H]+

Reference Synthesis Example 11

Synthesis of N$^5$-(4-hydroxy-3-sulfophenyl)-L-glutamine (Reference Compound No. 11)

Boc-Glu-OtBu (100 mg, 0.33 mmol) was dissolved in methylene chloride (1 ml) and THF (1 ml), and CDI (65 mg, 1.1 mmol) was added to the solution. The mixture was stirred for 30 minutes at room temperature. Sodium 5-amino-2-hydroxybenzenesulfonate (77 mg, 0.33 mmol) was added to the mixture and stirred overnight at room temperature. After the solvent was removed by distillation, the mixture was purified in accordance with the purification step A. The resulting intermediate was dissolved in 2 ml of TFA. After stirring for 3 hours at room temperature, the solvent was distilled off. The mixture was purified according to the purification step A to give the title compound.
Yield amount: 2 mg
ESI (m/z): 319 [M+H]+

Reference Synthesis Example 12

Synthesis of N$^5$-methyl-N$^5$-(3-sulfophenyl)-L-glutamine (Reference Compound No. 12)

Step 1: 3-[(2-nitrophenyl)sulfonyl]aminobenzenesulfonic acid

3-Aminobenzenesulfonic acid (346.3 mg, 2 mmol) was dissolved in 2.5 ml of methylene chloride. After cooling to 0° C., 2-nitrophenylbenzenesulfonyl chloride (443.2 mg, 2 mmol) and N,N-diisopropylethylamine (697 µl, 4 mmol) were added to the solution. After stirring at room temperature for an hour, the solvent was distilled off. The mixture was purified according to the purification step A to give the title compound.
Yield amount: 460 mg (1.29 mmol), yield: 64%
1H-NMR (DMSO-d6, 300 MHz): δ 7.02-7.83 (m, 8H)
ESI (m/z): 359 [M+H]+

Step 2: Synthesis of N$^5$-methyl-N$^5$-(3-sulfophenyl)-L-glutamine

Potassium carbonate (177 mg, 1.28 mmol), DMF (2 ml) and MeI (60 µl) were added to the compound (230 mg, 0.65 mmol) obtained in Step 1, followed by stirring at 40° C. for 6 hours. Potassium carbonate (44.3 mg) and MeI (40 µL) were supplemented and the mixture was stirred overnight. After the solvent was removed by distillation, the mixture was purified according to the purification step A to give the crude product of 3-{methyl[(2-nitrophenyl)sulfonyl]amino} benzenesulfonic acid (160 mg). This crude product (144 mg, 0.39 m ml) was dissolved in DMF (3 ml), and cesium carbonate (126 mg, 0.39 mmol) and thiophenol (40 μl, 0.39 mmol) were added to the solution. The mixture was stirred at 50° C. overnight. After the solvent was removed by distillation, the mixture was purified in accordance with the purification step A to give the crude product of 3-(methylamino)benzenesulfonic acid (84.1 mg).

The title compound was obtained in the same way except that the crude product of 3-(methylamino)benzenesulfonic acid was used in place of 3-sulfoaniline of REFERENCE SYNTHESIS EXAMPLE 1.

Yield amount: 5.14 mg
ESI (m/z): 317 [M+H]+

Reference Synthesis Example 13

Synthesis of O-{[(3-sulfophenyl)amino]carbonyl}-L-serine (Reference Compound No. 13)

Boc-Ser-OtBu (200 mg, 0.77 mmol) was dissolved in 3 ml of methylene chloride and cooled to 0° C. N,N'-carbonyldiimidazole (124 mg, 0.77 mmol) was added to the solution and stirred at room temperature for 2 hours. After the solvent was removed by distillation, 3-aminobenzenesulfonic acid (132.6 mg, 0.77 mmol), 2 ml of DMF and 0.4 ml of diisopropylethylamine were added and stirred at 70° C. overnight. The solvent was removed by distillation and the mixture was purified according to the purification step A to give the intermediate. The resulting intermediate was dissolved in 1 ml of TFA and stirred at room temperature for 2 hours. The solvent was removed by distillation, and the mixture was purified according to the purification step A to give the title compound.

Yield amount: 1.39 mg, yield: 0.6%
ESI (m/z): 304 [M+H]+

Reference Synthesis Example 14

Synthesis of 3-(L-γ-glutamylamino)benzoic acid (Reference Compound No. 14)

Boc-Glu-OtBu (100 mg, 0.33 mmol) and HATU (150.4 mg, 0.40 mmol) were dissolved in 2 ml of DMF, and triethylamine (68.5 μl) was added to the solution. The mixture was then stirred for 10 minutes. Ethyl 3-aminobenzoate (49.2 mg, 0.33 mmol) was added to the mixture and stirred overnight. After liquid separation was performed with ethyl acetate and 1M aqueous sodium hydroxide solution, the organic layer was washed sequentially with 1M aqueous sodium hydroxide solution, 1M hydrochloric acid and brine, followed by drying over sodium sulfate. After the solvent was distilled off, the resulting residue was dissolved in 2 ml of THF, 1 ml of ethanol and 1 ml of water, and lithium hydroxide monohydrate (13.5 mg, 0.32 mmol) was added to the solution. After stirring for 5 hours, 4.5 mg of lithium hydroxide was added to the mixture and stirred overnight. After it was confirmed that the reaction was completed, pH of the reaction solution was adjusted to 2 with 1M hydrochloric acid and the solvent was distilled off. After 3 ml of TFA was added to the resulting residue, the mixture was stirred at room temperature for 5 hours and the solvent was removed by distillation. The mixture was then purified according to the purification step A to give the title compound.

Yield amount: 54.17 mg, yield: 61%
1H-NMR (D$_2$O, 300 MHz): δ 7.92 (s, 1H), 7.72 (d, 1H, J=7.5 Hz), 7.55 (d, 1H, J=9 Hz), 7.42 (dd, 1H, J=7.5, 9.0 Hz), 4.00-3.80 (m, 1H), 2.58-2.54 (m, 2H), 2.20-2.15 (m, 2H)
ESI (m/z): 267 [M+H]+

Reference Synthesis Example 15

Synthesis of 3-(L-γ-glutamylamino)-2-hydroxybenzoic acid (Reference Compound No. 15)

The title compound was obtained in the same way except that ethyl 3-amino-2-hydroxybenzoate was used in place of ethyl 3-aminobenzoate of REFERENCE SYNTHESIS EXAMPLE 14.

Yield amount: 34.1 mg, yield: 37%
1H-NMR (D$_2$O, 300 MHz): δ 7.70-7.60 (m, 2H), 6.87 (t, 1H), 3.91 (t, 1H), 2.63-2.55 (m, 2H), 2.20-2.10 (m, 2H)
ESI (m/z): 283 [M+H]+

Reference Synthesis Example 16

Synthesis of 3-bromo-5-(L-γ-glutamylamino)benzoic acid (Reference Compound No. 16)

The title compound was obtained in the same way except that methyl 3-amino-5-bromobenzoate was used in place of ethyl 3-aminobenzoate of REFERENCE SYNTHESIS EXAMPLE 14.

Yield amount: 16.8 mg
1H-NMR (D$_2$O, 300 MHz): δ 7.80-7.85 (s*2, 2H), 3.75-3.90 (m, 1H), 2.45-2.55 (m, 2H), 2.10-2.20 (m, 2H)
ESI (m/z): 345, 347 [M+H]+

Reference Synthesis Example 17

Synthesis of N$^5$-{3-[hydroxy(methoxy)phosphoryl]phenyl}-L-glutamine (Reference Compound No. 17)

1-Iodo-3-nitrobenzene (249 mg, 1 mmol) was dissolved in 10 ml of acetonitrile, and tetrakistriphenylphosphine palladium (58 mg, 3 mol %), dimethyl phosphite (0.138 ml, 1.5 mmol) and triethylamine (0.28 ml, 2 mmol) were added to the solution. The mixture was stirred at 70° C. overnight. After the solvent was removed by distillation, the mixture was purified according to the purification step A to give the mixture of monomethyl and dimethyl (3-nitrophenyl)phosphonate (0.222 g). The resulting monomethyl phosphonate was dissolved in 10 ml of methanol and a catalytic amount of Pd/C was added thereto. The mixture was stirred in a hydrogen atmosphere overnight. The catalyst was filtered off and the solvent was removed by distillation to give the mixture of monomethyl and dimethyl (3-aminophenyl)phosphonate.

Boc-Glu-OtBu (303 mg, 1 mmol), HOAt (136 mg, 1 mmol) and HATU (380 mg, 1 mmol) were dissolved in 1 ml of DMF, and triethylamine (0.278 ml) was added to the solution. Ten minutes after, the mixture of monomethyl and dimethyl (3-aminophenyl)phosphonate was added to the mixture. The mixture was stirred at room temperature overnight.

After the solvent was distilled off, the mixture was purified according to the purification step A to give the title compound.

Yield amount: 11.5 mg
1H-NMR (D$_2$O, 300 MHz): δ 7.50-7.90 (m, 4H), 4.14-4.18 (m, 1H), 3.56 (s, 1.5H), 3.52 (s, 1.5H), 2.68-2.74 (m, 2H), 2.280-2.37 (m, 2H)
ESI (m/z): 317 [M+H]+

Reference Synthesis Example 18

Synthesis of N⁵-(3-phosphonophenyl)-L-glutamine (Reference Compound No. 18)

To a mixture (170 mg) of monomethyl and dimethyl (3-nitrophenyl)phosphonate obtained as the intermediate in REFERENCE SYNTHESIS EXAMPLE 17 were added 4 ml of DMF and trimethylsilyl bromide (1 ml). The mixture was stirred at 60° C. for 2 hours. After the solvent was removed by distillation, the residue was dissolved in a solvent mixture of water and methanol. A catalytic amount of Pd/C was added to the solution, and stirred overnight in a hydrogen atmosphere. The catalyst was filtered off and the solvent was removed by distillation to give the crude product of (3-aminophenyl)phosphonic acid.

Boc-Glu-OtBu (236 mg, 0.78 mmol), HOAt (127 mg, 0.936 mmol) and HATU (356 mg, 0.936 mmol) were dissolved in 1 ml of DMF, and triethylamine (0.21 ml) was added to the solution. Ten minutes after, the crude product of (3-aminophenyl)phosphonic acid was added and stirred at room temperature overnight. The solvent was distilled off and the mixture was purified in accordance with the purification step A to give the title compound.

Yield amount: 2.5 mg

ESI (m/z): 303 [M+H]+

Reference Synthesis Example 19

Synthesis of N⁵-(3-nitrophenyl)-L-glutamine (Compound No. 19)

The title compound was obtained in the same way except that 3-nitroaniline was used in place of 3-sulfoaniline of REFERENCE SYNTHESIS EXAMPLE 1.

Yield amount: 61.6 mg, yield: 93%

1H-NMR (DMSO-d6, 300 MHz): δ 10.5 (s, 1H), 8.66 (s, 1H), 7.86-7.93 (m, 2H), 7.61 (t, 1H, J=8.2 Hz), 3.99 (t, 1H, J=6.2 Hz), 2.50-2.70 (m, 2H), 2.06-2.16 (m, 2H)

ESI (m/z): 268 [M+H]+

Reference Synthesis Example 20

Synthesis of N-γ-glutamyl-aniline (Reference Compound No. 20)

Compound No. 20 used was purchased from Bachem Corp.

Hereinafter, synthesis of other representative compounds shown in TABLE 3 is described in more detail by referring to REFERENCE SYNTHESIS EXAMPLES. The compound of the present invention also includes, but not limited thereto, the compounds described in these REFERENCE SYNTHESIS EXAMPLES wherein the carboxyl group in the amino moiety is substituted with the E-CO— group.

TABLE 3

(I)

| Ref. Cpd. No. | $R^1$ | $R^2$ | $R^3$ | $R^4$ | $R^5$ | $R^6$ | X |
|---|---|---|---|---|---|---|---|
| 21 | H | SO₃H | Me | Cl | H | H | CH₂ |
| 22 | H | SO₃H | H | Cl | Me | H | CH₂ |
| 23 | OH | SO₃H | H | NO₂ | H | H | CH₂ |
| 24 | Cl | CO₂H | H | Cl | H | H | CH₂ |
| 25 | Cl | CO₂H | H | H | H | H | CH₂ |
| 26 | H | CO₂H | H | H | Cl | H | CH₂ |
| 27 | OMe | CO₂H | H | H | H | H | CH₂ |
| 28 | H | CO₂H | OH | H | H | H | CH₂ |
| 29 | H | CO₂H | H | H | Me | H | CH₂ |
| 30 | H | CO₂H | H | OH | H | H | CH₂ |
| 31 | Me | CO₂H | H | H | H | H | CH₂ |
| 32 | H | CO₂H | H | Cl | H | H | CH₂ |
| 33 | H | SO₃H | Me | Cl | H | H | O |
| 34 | OH | SO₃H | H | Cl | H | H | O |
| 35 | H | SO₃H | H | Cl | Me | H | O |
| 36 | OMe | SO₃H | H | Cl | H | H | O |
| 37 | H | SO₃H | H | H | Cl | H | CH₂ |
| 38 | H | H | SO₃H | Cl | H | H | CH₂ |
| 39 | SO₃H | H | H | Br | H | H | CH₂ |
| 40 | H | H | SO₃H | I | H | H | CH₂ |
| 41 | SO₃H | H | H | I | H | H | CH₂ |
| 42 | H | SO₃H | H | H | H | OH | CH₂ |
| 43 | H | SO₃H | H | H | H | OH | O |

Reference Synthesis Example 21

Synthesis of N⁵-(3-chloro-4-methyl-5-sulfophenyl)-L-glutamine (Reference Compound No. 21)

After 1 ml of methylene chloride and 1 ml of THF were added to 303 mg (1 mmol) of Boc-Glu-OtBu hydrochloride and 180 mg (1.1 mmol) of CDI, 221 mg of 5-amino-3-chloro-2-methylbenzenesulfonic acid was further added to mixture. The mixture was stirred at room temperature overnight and then purified in accordance with the purification step A to give the protected product. The protected product obtained was dissolved in 5 ml of trifluoroacetic acid. The solution was stirred for 2 hours. The solvent was distilled off and the mixture was purified in accordance with the purification step A to give the title compound.

1H-NMR (D₂O) δ: 7.71 (d, 1H), 7.60 (d, 1H), 3.93 (t, 1H), 2.50-2.57 (m, 2H), 2.47 (s, 3H), 2.10-2.20 (m, 2H)

ESI-MS: 349 [M−H]−, 351 [M+H]+

Reference Synthesis Example 22

Synthesis of N⁵-(3-chloro-2-methyl-5-sulfophenyl)-L-glutamine (Reference Compound No. 22)

After 2 ml of DMF and 0.52 ml (3 mmol) of DIEA were added to 303 mg (1 mmol) of Boc-Glu-OtBu hydrochloride, 221 mg (1 mmol) of 3-amino-5-chloro-4-methylbenzenesulfonic acid, 160 mg (1.3 mmol) of HOAt and 410 mg (1.3 mmol) of HATU, the mixture was stirred at room temperature overnight. The reaction solution was diluted in water-acetonitrile and purified in accordance with the purification step A to give the protected product. The protected product obtained was dissolved in 5 ml of trifluoroacetic acid and stirred for 2 hours. After the solvent was removed by distillation, the mixture was purified in accordance with the purification step A to give the title compound.

Yield amount: 150 mg

1H-NMR (D$_2$O) δ: 7.81 (d, 1H), 7.61 (d, 1H), 4.10 (t, 1H), 2.74-2.81 (m, 2H), 2.24-2.37 (m, 5H)

ESI-MS: 349 [M−H]−, 351 [M+H]+

Reference Synthesis Example 23

Synthesis of N$^5$-(2-hydroxy-5-nitro-3-sulfophenyl)-L-glutamine (Reference Compound No. 23)

The title compound was obtained in the same way except that 3-amino-2-hydroxy-5-nitrobenzenesulfonic acid was used in place of 3-amino-5-chloro-4-methylbenzenesulfonic acid of REFERENCE SYNTHESIS EXAMPLE 22.

Yield amount: 185 mg

1H-NMR (D$_2$O) δ: 8.55 (d, 1H, J=2.4 Hz), 8.29 (d, 1H, J=2.7 Hz), 3.95 (t, 1H, J=6.3 Hz), 2.66 (t, 2H, J=7.2 Hz), 2.10-2.30 (m, 2H)

ESI-MS: 362 [M−H]−, 364 [M+H]+

Reference Synthesis Example 24

Synthesis of 2,5-dichloro-3-(L-γ-glutamylamino)benzoic acid (Reference Compound No. 24)

(Step 1)

2,5-Dichloro-3-aminobenzoic acid, 206 mg (1.0 mmol), was dissolved in 4 ml of acetone, and 0.7 ml (1.4 mmol) of 2.0 M trimethylsilyl diazomethane solution in hexane was added to the solution. The mixture was stirred at room temperature for 1.5 hours. The solvent wad distilled off to give methyl 2,5-dichloro-3-aminobenzoate.

Yield amount: 220 mg (Step 2)

To 110 mg (0.5 mmol) of methyl 2,5-dichloro-3-aminobenzoate were added 190 mg (0.5 mmol) of HATU, 70 mg (0.5 mmol) of HOAt, 152 mg (0.5 mmol) of Boc-Glu-OtBu hydrochloride, 0.21 ml (1.5 mmol) of triethylamine and 2 ml of dichloromethane. The mixture was stirred at room temperature overnight.

The solvent was distilled off, and extraction was performed with ethyl acetate-water. The organic layer was treated with brine and dried over sodium sulfate. Sodium sulfate was removed by filtration. After the solvent was removed by distillation, 5 ml of 1N sodium hydroxide solution was added and stirred at room temperature for 2 hours. Subsequently, 5 ml of trifluoroacetic acid was added and stirred at room temperature for 2 hours. The solvent was distilled off, and the mixture was purified in accordance with the purification step A to give the title compound.

Yield amount: 6.6 mg

1H-NMR (CD3OD) δ: 8.08 (s, 1H), 7.56 (s, 1H), 3.95-4.01 (m, 1H), 2.76-2.82 (m, 2H), 2.20-2.30 (m, 2H)

ESI-MS: 333 [M−H]−, 335 [M+H]+

Reference Synthesis Example 25

Synthesis of 2-chloro-3-(L-γ-glutamylamino)benzoic acid (Reference Compound No. 25)

The title compound was obtained in the same way except that 2-chloro-3-aminobenzoic acid was replaced for the benzoic acid derivative used in REFERENCE SYNTHESIS EXAMPLE 24 (Synthesis of Compound No. 24).

Yield amount: 4.0 mg

1H-NMR (D$_2$O) δ: 7.47-7.56 (m, 1H), 7.39-7.46 (m, 1H), 7.27-7.32 (s, 1H), 3.81-387 (m, 1H), 2.59-2.65 (m, 2H), 2.12-2.21 (m, 2H)

ESI-MS: 299 [M−H]−, 301 [M+H]+

Reference Synthesis Example 26

Synthesis of 4-chloro-3-(L-γ-glutamylamino)benzoic acid (Reference Compound No. 26)

The title compound was obtained in the same way except that 4-chloro-3-aminobenzoic acid was replaced for the benzoic acid derivative used in REFERENCE SYNTHESIS EXAMPLE 24 (Synthesis of Compound No. 24).

Yield amount: 5.3 mg

1H-NMR (D$_2$O) δ: 8.03 (s, 1H), 7.76-7.79 (m, 1H), 7.52-7.55 (m, 1H), 3.78-3.84 (m, 1H), 2.59-2.65 (m, 2H), 2.12-2.22 (m, 2H)

ESI-MS: 299 [M−H]−, 301 [M+H]+

Reference Synthesis Example 27

Synthesis of 2-methoxy-3-(L-γ-glutamylamino)benzoic acid (Reference Compound No. 27)

HATU, 84 mg (0.2 mmol), 30 mg (0.2 mmol) of HOAt, 61 mg (0.2 mmol) of Boc-Glu-OtBu hydrochloride, 0.084 ml (0.6 mmol) of triethylamine and 1 ml of dichloromethane were added to 36 mg (0.2 mmol) of methyl 2-methoxy-3-aminobenzoate. The mixture was stirred at room temperature overnight.

The solvent was distilled off, and extraction was performed with ethyl acetate-water. The organic layer was treated with brine and dried over sodium sulfate. Sodium sulfate was removed by filtration. After the solvent was removed by distillation, 5 ml of 1N aqueous sodium hydroxide solution was added and stirred at room temperature for 2 hours. Subsequently, 5 ml of trifluoroacetic acid was added to the mixture. The mixture was stirred at room temperature for 2 hours. The solvent was distilled off, and the mixture was purified according to the purification step A to give the title compound.

Yield amount: 6.5 mg

1H-NMR (D$_2$O) δ: 7.69-7.71 (m, 1H), 7.56-7.59 (m, 1H), 7.13-7.18 (m, 1H), 3.87-3.93 (m, 1H), 3.68 (s, 3H), 2.60-2.66 (m, 2H), 2.12-2.22 (m, 2H)

ESI-MS: 295 [M−H]−, 297 [M+H]+

Reference Synthesis Example 28

Synthesis of 6-hydroxy-3-(L-γ-glutamylamino)benzoic acid (Reference Compound No. 28)

6-Methoxy-3-(L-γ-glutamylamino)benzoic acid was synthesized in the same way except that 6-methoxy-3-aminobenzoic acid was replaced for the benzoic acid derivative used in REFERENCE SYNTHESIS EXAMPLE 27 (Synthesis of Compound No. 27). The product was purified according to the purification step A to give the title compound as a by-product obtained in the course of synthesis.

Yield amount: 2.1 mg

ESI-MS: 280 [M−H]−, 282 [M+H]+

Reference Synthesis Example 29

Synthesis of
4-methyl-3-(L-γ-glutamylamino)benzoic acid
(Reference Compound No. 29)

4-Methyl-3-nitrobenzoic acid, 500 mg, was dissolved in 5 ml of methanol and 10 ml of 4N hydrogen chloride-containing dioxane solution. After stirring for 2 days at room temperature, the solvent was distilled off to give the crude product. The crude product obtained was dissolved in 10 ml of methanol, and a catalytic amount of Pd/C was reacted at room temperature overnight in a hydrogen atmosphere. The catalyst was removed by filtration and the solvent was distilled off to give the crude product. After 165 mg of the crude product, 303 mg (1 mmol) of Boc-Glu-OtBu hydrochloride and 400 mg (ca 1.3 mmol) of HATU were dissolved in 1 ml of DMF, 0.26 ml of DIEA was added to the solution and stirred overnight. The reaction solution was diluted in water-acetonitrile and the mixture was purified in accordance with the purification step A to give 0.31 g of the protected product. To the protected product obtained were added 3 ml of THF, 1.5 ml of methanol and 1.5 ml of water. Then, 26 mg (0.82 mmol) of lithium hydroxide monohydrate was added to the mixture. After stirring for 2 hours, the solvent was distilled off. Again, 3 ml of THF, 1.5 ml of methanol and 1.5 ml of water were added and, 26 mg (0.82 mmol) of lithium hydroxide monohydrate was further added to the mixture. The mixture was stirred for 2 hours. After 2 ml of ethyl acetate was added, the solvent was distilled off. Next, 3 ml of trifluoroacetic acid was added and stirred at room temperature for 2 hours. The solvent was removed by distillation, and the mixture was purified according to the purification step A to give the title compound.

1H-NMR (D$_2$O) δ: 7.74-7.77 (m, 1H), 7.30-7.36 (m, 1H), 3.75-3.81 (m, 1H), 2.55-2.62 (m, 2H), 2.10-2.20 (m, 5H)

ESI-MS: 279 [M−H]−, 281 [M+H]+

Reference Synthesis Example 30

Synthesis of
5-hydroxy-3-(L-γ-glutamylamino)benzoic acid
(Reference Compound No. 30)

5-Methoxy-3-(L-γ-glutamylamino)benzoic acid was obtained in the same way except that 5-methoxy-3-aminobenzoic acid was replaced for the benzoic acid derivative used in REFERENCE SYNTHESIS EXAMPLE 27 (Synthesis of Compound No. 27). The product was purified according to the purification step A to give the title compound as a by-product obtained in the course of synthesis.

Yield amount: 7.5 mg

ESI-MS: 280 [M−H]−, 282 [M+H]+

Reference Synthesis Example 31

Synthesis of
3-(L-γ-glutamylamino)-2-methylbenzoic acid
(Reference Compound No. 31)

The title compound was obtained in the same way except that 2-methyl-3-nitrobenzoic acid was replaced for the benzoic acid derivative used in REFERENCE SYNTHESIS EXAMPLE 29 (Synthesis of Reference Compound No. 29).

Yield amount: 37 mg

1H-NMR (D$_2$O) δ: 7.56 (dd, 1H), 7.30 (dd, 1H), 7.23 (t, 1H), 3.82 (t, 1H), 2.5-2.62 (m, 2H), 2.21 (s, 3H), 2.10-2.29 (m, 2H)

ESI-MS: 279 [M−H]−, 281 [M+H]+

Reference Synthesis Example 32

Synthesis of 5-chloro-3-(L-γ-glutamylamino)benzoic acid (Reference Compound No. 32)

(Step 1)

After 8 ml of methanol and 2 ml of THF were added to 228 mg (1 mmol) of methyl 5-chloro-1,3-dibenzoate and 56 mg (1 mmol) of potassium hydroxide, the mixture was stirred at room temperature overnight. The reaction solution was concentrated under reduced pressure. Then, 4 ml of toluene, 0.12 ml (0.85 mmol) of triethylamine and 0.19 ml (0.88 mmol) of diphenylphosphorylazide were added and stirred at 50° C. for an hour. Subsequently, 0.19 ml (2 mmol) of t-butyl alcohol and 2 ml of toluene were added and stirred at 80° C. overnight. After cooling to room temperature, the mixture was extracted with ethyl acetate-water. The organic layer was treated with brine and dried over sodium sulfate. Sodium sulfate was removed by filtration. The solvent was removed by distillation, and the mixture was purified in accordance with the purification step A to give methyl 5-chloro-3-aminobenzoate-trifluoroacetate.

Yield amount: 30 mg (Step 2)

HATU, 38 mg (0.1 mmol), 14 mg (0.1 mmol) of HOAt, 30 mg (0.1 mmol) of Boc-Glu-OtBu hydrochloride, 0.014 ml (0.1 mmol) of triethylamine and 1 ml of dichloromethane were added to 30 mg (0.1 mmol) of methyl 5-chloro-3-aminobenzoate. The mixture was stirred at room temperature overnight.

The solvent was removed by distillation, followed by extraction with ethyl acetate-water. The organic layer was treated with brine and then dried over sodium sulfate. Sodium sulfate was removed by filtration. After the solvent was removed by distillation, 5 ml of 1N sodium hydroxide solution was added and stirred at room temperature for 2 hours. Subsequently, 5 ml of trifluoroacetic acid was added and stirred at room temperature for 2 hours. After the solvent was removed by distillation, the mixture was purified according to the purification step A to give the title compound.

Yield amount: 1.0 mg

1H-NMR (D$_2$O) δ: 7.54 (s, 1H), 7.48 (s, 1H), 7.45 (s, 1H), 3.96-4.00 (m, 1H), 2.50-2.56 (m, 2H), 2.12-2.20 (m, 2H)

ESI-MS: 299 [M−H]−, 301 [M+H]+

Reference Synthesis Example 33

Synthesis of O-{[(3-chloro-4-methyl-5-sulfophenyl)amino]carbonyl}-L-serine (Reference Compound No. 33)

Boc-Ser-OtBu, 100 mg (0.38 mmol), 86 mg (0.38 mmol) of 5-amino-3-chloro-2-methylbenzenesulfonic acid and 37 mg (0.0127 mmol) of triphosgene were suspended in 1 ml of methylene chloride, and 66 μl (0.76 mmol) of DIEA was added to the suspension. After stirring at room temperature overnight, the solvent was removed by distillation. The mixture was purified according to the purification step A to give the protected title compound. The resulting protected product was dissolved in 2 ml of trifluoroacetic acid and stirred for 2 hours. The solvent was removed by distillation and the mixture was purified according to the purification step A to give the title compound.

Yield amount: 15.5 mg

1H-NMR (D$_2$O) δ: 7.67 (d, 1H), 7.57. (d, 1H), 4.51 (t, 2H), 4.15 (dd, 1H) 2.47 (s, 3H)

ESI-MS: 351 [M−H]−, 353 [M+H]+

Reference Synthesis Example 34

Synthesis of sodium 3-({[(2S)-2-amino-2-carboxyethoxycarbonyl}amino)-5-chloro-2-hydroxy-benzenesulfonate (Reference Compound No. 34)

The title compound was obtained in the same way except that 3-amino-5-chloro-2-hydroxybenzenesulfonic acid was replaced for the benzenesulfonic acid derivative used in REFERENCE SYNTHESIS EXAMPLE 33 (Synthesis of Reference Compound No. 33), then 1 equivalent of 0.1N sodium hydroxide aqueous solution was added and freeze dried.

Yield amount: 15.1 mg

1H-NMR (D$_2$O) δ: 7.70 (s, 1H), 7.37 (d, 1H, J=2.6 Hz), 4.37-4.55 (m, 2H), 3.98 (dd, 1H, J=3.0, 5.3 Hz),

ESI-MS: 353 [M−H]−, 355 [M+H]+

Reference Synthesis Example 35

Synthesis of O-{[(3-chloro-2-methyl-5-sulfophenyl)amino]carbonyl}-L-serine (Reference Compound No. 35)

The title compound was obtained in the same way except that 3-amino-5-chloro-4-methylbenzenesulfonic acid was replaced for the benzenesulfonic acid derivative used in REFERENCE SYNTHESIS EXAMPLE 33 (Synthesis of Reference Compound No. 33).

Yield amount: 3.9 mg

1H-NMR (D$_2$O) δ: 7.60-7.64 (m, 2H), 4.42-4.54 (m, 2H), 4.03 (dd, 1H, J=3.2, 4.8 Hz)

ESI-MS: 351 [M−H]−, 353 [M+H]+

Reference Synthesis Example 36

Synthesis of O-{[(5-chloro-2-methoxy-3-sulfophenyl)amino]carbonyl}-L-serine (Reference Compound No. 36)

Acetone (2 ml) was added to 30 mg of the protected product obtained in REFERENCE SYNTHESIS EXAMPLE 14 (Synthesis of Reference Compound No. 14), and 1 ml of 2M trimethylsilyldiazomethane-containing hexane solution and 100 μl of triethylamine were further added to the mixture. After stirring for 20 minutes, the solvent was removed by distillation. The mixture was purified according to the purification step A to give the methylated product. The methylated product obtained was dissolved in 2 ml of trifluoroacetic acid and stirred at room temperature for 3 hours. After the solvent was removed by distillation, water was added and freeze dried to give the title compound.

Yield amount: 1.48 mg

1H-NMR (D$_2$O) δ: 7.64 (brs, 1H), 7.27 (d, 1H, J=2.6 Hz), 4.25-4.22 (m, 2H), 3.80 (dd, 1H, J=3.1, 5.0 Hz), 3.52 (s, 3H)

Reference Synthesis Example 37

Synthesis of N$^5$-(2-chloro-5-sulfophenyl)-L-glutamine (Reference Compound No. 37)

To sodium 4-chloro-3-nitrobenzenesulfonate (1 mmol) were added 2 ml of methanol and 3 ml of water. A catalytic amount of 2% Pt—S/C was added to the mixture, followed by stirring at room temperature overnight in a hydrogen atmosphere. The catalyst was removed by filtration. After sufficiently drying, 303 mg (1 mmol) of Boc-Glu-OtBu hydrochloride, 163 mg (1.2 mmol) of HOAt, 456 mg (1.2 mmol) of HATU, 2 ml of DMF and 0.35 ml of DIEA were added and stirred at room temperature overnight. The reaction solution was diluted in water-acetonitrile and purified according to the purification step A to give the protected title compound. The resulting protected product was dissolved in 3 ml of trifluoroacetic acid and stirred at room temperature for 2 hours. The solvent was removed by distillation. The mixture was then purified according to the purification step A to give the title compound.

Yield amount: 69.9 mg

1H-NMR (D$_2$O) δ: 7.85 (brs, 1H), 7.50-7.55 (m, 2H), 4.03 (t, 1H), 2.66 (t, 2H, J=7.1 Hz), 2.10-2.30 (m, 2H)

ESI-MS: 335 [M−H]−, 337 [M+H]+

Reference Synthesis Example 38

Synthesis of N$^5$-(3-chloro-4-sulfophenyl)-L-glutamine (Reference Compound No. 38)

Step 1

3-Chloroaniline, 0.4 ml, was slowly added to 4 ml of fuming sulfuric acid and stirred at room temperature overnight. While cooling to 0°, the reaction solution was poured onto water and the solid precipitated was separated by filtration. The solid filtered was dissolved in 2N sodium hydroxide aqueous solution and conc. hydrochloric acid was then added to the solution to make the liquid acidic. The solid precipitated was taken by filtration to give the crude product of 4-amino-2-chlorobenzenesulfonic acid.

Yield amount: 80 mg

Step 2

The title compound was obtained in the same way except that the crude product of 4-amino-2-chlorobenzenesulfonic acid obtain in Step 1 was replaced for the benzenesulfonic acid derivative used in REFERENCE SYNTHESIS EXAMPLE 21 (Synthesis of Reference Compound No. 21).

Yield amount: 40 mg

1H-NMR (D$_2$O) δ: 7.80 (d, 1H), 7.63 (d, 1H), 7.33 (dd, 1H), 3.94 (t, 1H), 2.50-2.60 (m, 2H), 2.10-2.22 (m, 2H)

ESI-MS: 337 [M+H]+, 335 [M−H]−

Reference Synthesis Example 39

Synthesis of N$^5$-(5-bromo-3-sulfophenyl)-L-glutamine (Reference Compound No. 39)

The title compound was obtained in the same way as in Steps 1 and 2 except that 3-bromoaniline was replaced for the aniline derivative used in Step 1 of REFERENCE SYNTHESIS EXAMPLE 18 (Synthesis of Reference Compound No. 18).

Yield amount: 9.9 mg

ESI-MS: 429 [M+H]+, 427 [M−H]−

Reference Synthesis Example 40

Synthesis of $N^5$-(3-iodo-4-sulfophenyl)-L-glutamine (Reference Compound No. 40)

The title compound was obtained in the same way as in Steps 1 and 2 except that 3-iodoaniline was replaced for the aniline derivative used in Step 1 of REFERENCE SYNTHESIS EXAMPLE 38 (Synthesis of Reference Compound No. 38).

Yield amount:
1H-NMR ($D_2O$) δ: 8.12 (s, 1H), 7.84 (d, 1H), 7.44 (dd, 1H), 3.75-3.90 (m, 1H), 2.50-2.60 (m, 2H), 2.00-2.20 (m, 2H)
ESI-MS: 429 [M+H]+, 427 [M−H]−

Reference Synthesis Example 41

Synthesis of $N^5$-(5-iodo-2-sulfophenyl)-L-glutamine (Reference Compound No. 41)

The product was obtained as a regioisomer in the synthesis of REFERENCE SYNTHESIS EXAMPLE 40.

Yield amount:
1H-NMR ($D_2O$) δ: 8.11 (d, 1H), 7.63-7.66 (m, 1H), 7.48 (d, 1H), 3.80-3.90 (m, 1H), 2.58-2.66 (m, 2H), 2.10-2.24 (m, 2H)
ESI-MS: 429 [M+H]+, 427 [M−H]−

Reference Synthesis Example 42

Synthesis of $N^5$-hydroxy-$N^5$-(3-sulfophenyl)-L-glutamine (Reference Compound No. 42)

Zinc powders, 270 mg (4.3 mmol) and 106 mg (2 mmol) of ammonium chloride were suspended in 2 ml of a solvent mixture of methanol:water (1:1), and 450 mg (2 mmol) of sodium 2-nitrobenzenesulfonate was slowly added to the suspension. After one hour stirring at 65° C., insolubles were removed by filtration and the resulting filtrate was distilled off to give the crude product of the hydroxylamine derivative. After 5 ml of DMF and 0.35 ml of DIEA were added to 450 mg (1.5 mmol) of Boc-Glu-OtBu hydrochloride, 230 mg (1.7 mmol) of HOAt and 646 mg (1.7 mmol) of HATU, the mixture was stirred for 10 minutes. The solution was added to the crude product previously obtained, followed by stirring overnight. The mixture was purified according to the purification step A to give the protected title compound. After 4 ml of TFA was added to the resulting protected product, the mixture was stirred for 2 hours. TFA was removed and the mixture was purified according to the purification step A to give the title compound.

Yield amount: 135 mg
1H-NMR (DMSO) δ: 10.65 (s, 1H), 10.04 (s, 1H), 7.20-8.40 (m, 7H), 3.90-4.10 (m, 1H), 2.60-3.00 (m, 2H), 1.90-2.20 (m, 2H)
ESI-MS: 317 [M−H]−, 319 [M+H]+

Reference Synthesis Example 43

Synthesis of O-{[hydroxy(3-sulfophenyl)amino]carbonyl}-L-serine (Reference Compound No. 43)

Methylene chloride, 2 ml, and 0.35 ml of DIEA were added to 1 mmol of Boc-Ser-OtBu, the crude product of hydroxylamine obtained in SYNTHESIS EXAMPLE 42 and 100 mg (0.33 mmol) of triphosgene, followed by stirring at room temperature overnight. The solvent was removed by distillation. The resulting residue was purified according to the purification step A to give the protected title compound. The protected product obtained was dissolved in 4 ml of TFA and stirred at room temperature for 3 hours. TFA was removed by distillation, and the mixture was then purified according to the purification step A to give the title compound.

Yield amount: 6.6 mg
1H-NMR ($D_2O$) δ: 7.78-7.80 (m, 1H), 7.43-7.60 (m, 4H), 4.56-4.58 (m, 2H), 4.10-4.15 (m, 1H)
ESI-MS: 319 [M−H]−, 321 [M+H]+

Example II

Evaluation of CaSR Agonist Activity (Preparation of Gene for CaSR)

The gene for CaSR was prepared by the method described in Example 1 of WO 07/55393. Using the recombinant plasmid obtained, human CaSR expression plasmid hCaSR/pcDNA3.1 was prepared.

(Evaluation of CaSR Agonist)

293E cells (HEK293 cell expressing EBNA1, ATCC No. CRL-10852) were cultured in DMEM (Dulbecco's Modified Eagle's Medium containing 1.0 g/ml glucose, NACALAI TESQUE, INC.) containing 10% fetal calf serum, in the presence of 250 μg/ml of G418. The cells were spread on a Petri dish of 10 cm diameter in $1.8 \times 10^6$ cells/15 ml. After the cells were allowed to stand in a $CO_2$ incubator (5% $CO_2$, 37° C.) for 24 hours, plasmid expressing human CaSR, i.e., hCaSR/pcDNA3.1 was transfected with a transfection reagent Mirus TransIT 293 (Takara Bio Inc.). After the cells were allowed to stand in the $CO_2$ incubator for 24 hours, the cells were collected by DMEM containing 10% fetal calf serum and plated on poly-D-lysine coated 384 well plate (Falcon) in 15,000 cells/well. After the cells were allowed to stand in the $CO_2$ incubator for 24 hours, the medium was removed. Then, 50 μL/well of $Ca^{2+}$ fluorescence indicator Calcium 4 Assay Kit (Molecular Devices) that was dissolved in an assay buffer (146 mM NaCl, 5 mM KCl, 1 mM $MgSO_4$, 1 mg/ml glucose, 20 mM HEPES (pH 7.2), 1.5 mM $CaCl_2$) was added thereto, and allowed to stand at 37° C. for an hour and at room temperature for 30 minutes to load the fluorescence indicator. The 384 well plate was transferred to FLIPR (Molecular Devices). Then, 12.5 μL/well of a compound that was dissolved in a 0.1% BSA containing-assay buffer was added thereto, and change in fluorescence intensity was measured for 3 minutes. Meanwhile, Compound No. 20 was purchased from Bachem.

(Method for Calculating $EC_{50}$)

The difference between the maximum and minimum fluorescent intensities (RFU (Max−Min)) observed for each well before and after the addition of a test compound was determined by the automatic calculation using FLIPR. The activity rate was calculated based on the RFU (Max−Min) value observed when adding the compound at the maximum concentration being defined as 100% and the RFU (Max−Min) value observed when adding DMSO instead of the compound at the same concentration being defined as 0%. The resulting data was then input to the curve-fitting procedures using the spreadsheet software XLfit to determine the $EC_{50}$ that is a concentration of the compound at the activity rate of 50%. The results of the compounds of the present invention listed in TABLE 1 are shown in TABLE 4. The results of the reference compounds listed in TABLES 2 and 3 are shown in TABLES 5 and 6.

TABLE 4

| EXAMPLE No. | EC$_{50}$ (μM) |
| --- | --- |
| 1 | 0.023 |
| 6 | 0.11 |
| 7 | 0.004 |

TABLE 5

| Reference Compound No. | EC$_{50}$ [μM] |
| --- | --- |
| 1 | 0.012 |
| 2 | 2.3 |
| 3 | 0.56 |
| 4 | 0.059 |
| 5 | 0.13 |
| 6 | 2.7 |
| 7 | 0.0019 |
| 8 | 0.10 |
| 9 | 0.27 |
| 10 | 0.017 |
| 11 | 0.086 |
| 12 | 0.20 |
| 13 | 0.072 |
| 14 | 2.0 |
| 15 | 0.034 |
| 16 | 0.048 |
| 17 | 2.0 |
| 18 | 0.53 |
| 19 | 0.40 |
| 20 | 0.94 |

TABLE 6

| Reference Compound No. | EC$_{50}$ [μM] |
| --- | --- |
| 21 | 0.0057 |
| 22 | 0.0014 |
| 23 | 0.89 |
| 24 | 0.022 |
| 25 | 0.97 |
| 26 | 0.16 |
| 27 | 0.15 |
| 28 | 0.33 |
| 29 | 0.53 |
| 30 | 2.9 |
| 31 | 3.7 |
| 32 | 0.0088 |
| 33 | 0.0021 |
| 34 | 0.0019 |
| 35 | 0.0037 |
| 36 | 3.5 |
| 37 | 0.0029 |
| 38 | 6.7 |
| 39 | 5.0 |
| 40 | 7.9 |
| 41 | 2.3 |
| 42 | 0.031 |
| 43 | 0.043 |

Example III

Effect of CaSR Agonist on Water Absorption in Rat Large Intestine Loop Method (1)

(Method)

Under pentobarbital anesthesia the cecum and large intestine were isolated from the abdomen of a male SD (IGS) rat, and a large intestine loop was prepared by ligating a point 5 cm just below the cecum. Immediately after preparing the loop, PGE2 (4 μg/ml/kg, SIGMA) was intraperitoneally administered. Thirty minutes later, 2 ml of Tyrode solution (136.9 mM NaCl, 2.7 mM KCl, 1.8 mM $CaCl_2.2H_2O$, 1.04 mM $MgCl_2.6H_2O$, 0.04 mM $NaH_2PO_4.2H_2O$, 5.55 mM glucose and 11.9 mM $NaHCO_3$) was poured into the loop prepared. An hour later, the weight of the loop, the weight when the liquid was removed from the loop and the loop area were measured to calculate the weight per unit area of the liquid that remains in the loop.

A test compound was dissolved in Tyrode solution (adjusted to pH 6.5 to 7.5), which was provided for tests.

The remaining liquid weight per unit area (g/cm$^2$) was calculated by the following equation.

Remaining liquid weight per unit area (g/cm$^2$)=(loop weight−loop weight when the liquid was removed from the loop)/loop area Water absorption was evaluated by calculating the inhibition ratio by the following equation.

Inhibition ratio(%)=100−(remaining liquid weight per unit area with a drug−basic average remaining liquid weight per unit area)/(average remaining liquid weight per unit area of vehicle−basic average remaining liquid weight per unit area)×100

The results are shown in FIG. 1. Water absorption of Reference Compound No. 1 in TABLE 2 was promoted dose-dependently, suggesting that the compound is useful as a therapeutic or preventive agent for diarrhea. As stated above, the group shown by E-CO in formula (I) can be converted into a carboxyl group in vivo and it is considered that the compound in which the carboxyl group in the amino acid moiety of the reference compound is replaced by the E-CO group would exhibit the effects as a therapeutic or preventive agent for diarrhea as it is or through conversion of the E-CO group into a carboxyl group.

Example IV

Effect of CaSR Agonist on Water Absorption in Rat Large Intestine Loop Method (2)

Figure 2:
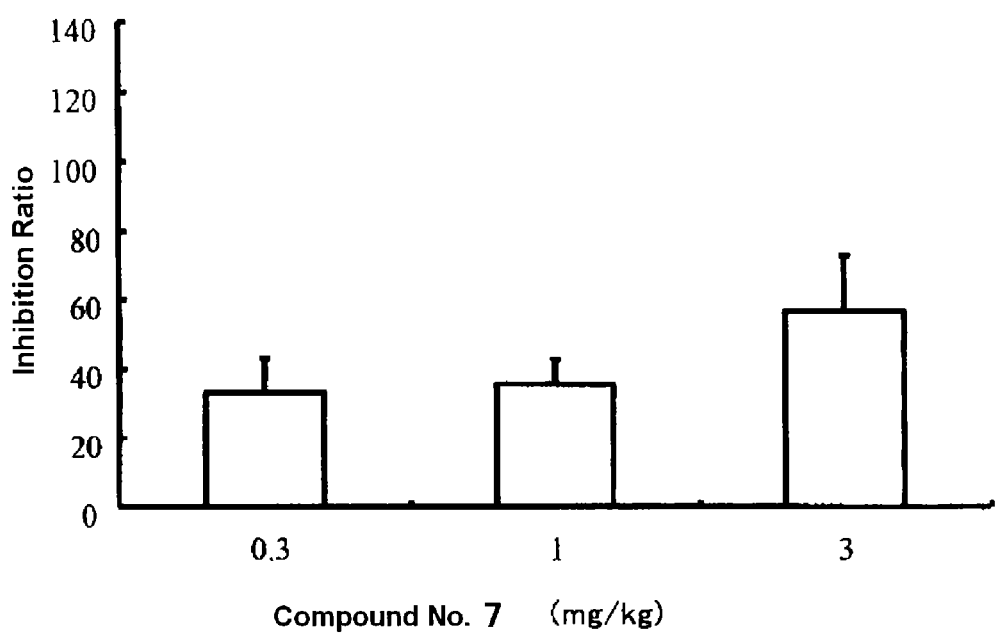
FIG. 2 shows the preventive activity of Reference Compound No. 7 against diarrhea.

The same test as the method of Example IV was conducted on Compound No. 7. The results are shown in FIG. 2. The water absorption of Compound No. 7 in TABLE 1 was promoted in a dose-dependent manner, suggesting that the compound is useful as a therapeutic or preventive agent for diarrhea. As stated above, it is thus considered that the compound in which the carboxyl group in the amino acid moiety of the reference compound is replaced by the E-CO group would exhibit the effects as a therapeutic or preventive agent for diarrhea as it is or through conversion of the E-CO group into a carboxyl group.

Example V (Text Example 1) Evaluation of Kokumi Taste

<Kokumi-Imparting Activity of Compounds (Sodium Salts of Reference Compound Nos. 1, 7 and 21) used in the Present Invention>

On the compounds in which the calcium receptor activating action was found (sodium salts of Compound Nos. 1, 7 and 21), the intensity of kokumi-imparting activity was examined by a quantitative sensory evaluation test. In 5 ml of distilled water was dissolved 525 mg of Compound No. 1 described in REFERENCE EXAMPLE I and of REFERENCE SYNTHESIS EXAMPLE I. By adding 16.4 ml of 0.1M sodium hydroxide solution to the resulting solution, the solution was adjusted to pH 6.5 to 7 followed by freeze-drying. The resulting Na salt was provided for use. In addition, 500 mg of Compound No. 7 described in REFERENCE EXAMPLE I and REFERENCE SYNTHESIS EXAMPLE 7 was suspended in 5 ml of distilled water. To the suspension were sequentially added 1.61 ml of 1M sodium hydroxide and 0.8 ml of 2M hydrochloric acid at 0° C. The solid precipitated was taken out by filtration and dried under reduced pressure at 40° C. to give 426 mg of Reference Compound No. 7. After the solid substance obtained was suspended in 10 ml of distilled water, 1.2 ml of 1M sodium hydroxide was added to the suspension and freeze-dried. The resulting Na salt was provided for use. Reference Compound No. 21 was used in the form of the Na salt, which was prepared from Compound No. 21 described in REFERENCE EXAMPLE I and REFERENCE SYNTHESIS EXAMPLE 21 by the same procedures as described above.

A quantitative sensory evaluation test was conducted as follows. The intensity of kokumi-imparting activity was examined when 0.000001 to 0.1 g/dl of the compound as a sample (No. 1—Na salt) was mixed with distilled water containing sodium glutamate (0.05 g/dl), inosine monophosphate (0.05 g/dl) and sodium chloride (0.5 g/dl). As a reference, γGlu-Cys-Gly and γGlu-Val-Gly were used, each of which is a known kokumi-imparting component. The sample that became acidic to an additive-free control after dissolving the sample was used by adjusting its pH within ±0.2 with NaOH based on the additive-free control. Sensory scoring was defined as a control: 0, strong: 3 and very strong: 5, and performed in n=4. Meanwhile, a "first-middle taste" is intended to mean the taste combining the first taste and middle taste. The kokumi-imparting activity was widely found in the above concentrations for addition. The results of representative concentrations are shown in TABLE 7.

TABLE 7

| Sample | Concentration (g/dl) | Kokumi Intensity First-middle taste | Aftertaste | Comments on Sensory Evaluation |
|---|---|---|---|---|
| Control | — | 0 | 0 | — |
| γGlu-Cys-Gly | 0.01 | 3.0 | 3.0 | Richness, thickness and continuity were enhanced. |
| γGlu-Val-Gly | 0.001 | 2.5 | 3.0 | Smoothness, richness and growth (mouthfulness) were mainly enhanced. |
|  | 0.005 | 3.5 | 4.0 | Smoothness, richness and growth (mouthfulness) were mainly enhanced. |
| No. 1-Na salt | 0.00001 | 0.7 | 1.0 | Though there is thickness, it is not enough. |
|  | 0.0001 | 1.8 | 2.0 | There was harmony accompanied by a bit of thickness. |
|  | 0.0005 | 2.6 | 3.0 | There were harmony, richness and thickness. |
|  | 0.001 | 3.2 | 3.6 | Thickness and continuity were mainly enhanced, though all tastes were strong. |
|  | 0.01 | 5.0 | 5.0 | All tastes were strong. |
| No. 7-Na salt | 0.00005 | 2.2 | 2.5 | Thickness mainly in the middle taste. |
|  | 0.0001 | 2.5 | 3.2 | Almost the same thickness as that achieved by 0.001 γGlu-Val-Gly. |
|  | 0.0005 | 3.3 | 4.0 | Rich thickness in the middle taste and strong aftertaste. |
| No. 21-Na salt | 0.0002 | 1.5 | 2.0 | Richness was added a bit but weak. |
|  | 0.0005 | 2.6 | 3.1 | Richness was added and both umami and sweetness were enhanced. |
|  | 0.001 | 3.1 | 3.7 | Richness was strong but accompanied by a bit of bitterness and the taste was blurred. |

As described above, the compounds in which the carboxyl group in the amino acid moiety of reference compounds is replaced by the E-CO group are considered to exhibit the effect as the kokumi imparting agent directly as it is or through conversion of the E-CO group into the carboxyl group.

Example VI

Activity of Lowering iPTH (Intact Parathyroid Hormone) by Intravenous Bolus Administration in Rats (Method)

The compound of the present invention is bolus administered to male SD (IGS) rat via tail vein to monitor changes in concentration of serum iPTH and serum Ca. Blood is collected prior to the administration and 5, 15, 30 and 60 minutes after the administration.

The compound of the present invention is dissolved in physiological saline at a concentration of approximately 0.001 to 10 mg/ml.

Cinacalcet as a reference drug is dissolved in a solution of PEG400:saline=1:1.

It can be confirmed that the compound of the present invention exhibits the activity of lowering serum iPTH and serum Ca and is useful as a preventive or therapeutic agent for hyperparathyroidism.

Example VII

Effect on Non-Steroidal Antiinflammatory Drug (NSAID)-Induced Enteritis (Method)

The compound of the invention is orally administered to non-starved rats in 1 to 50 mg/kg. Loxoprofen (60 mg/kg) is then orally administered 30 minutes after and the animal is held for 24 hours. Thirty (30) minutes before autopsy, 1 ml of 1% (w/w) Evans Blue is intravenously injected. After the animals were sacrificed under deep ether anesthesia to isolate the small intestine (from the duodenum to the ileum) of the test objects, the small intestine is soaked in 2% formalin for 10 minutes, fixed from the serous membrane side and dissected from the opposite side of the mesenterium. The injured area of the small intestine ($mm^2$) was measured under a dissecting microscope with ×10 magnification.

It can be confirmed that the compound of the present invention improves the injured area. It can thus be confirmed that the compound of the present invention is useful as a preventive or therapeutic agent for peptic ulcer.

INDUSTRIAL APPLICABILITY

The present invention is useful in the medical field, specifically in the field relating to a disease with pathological conditions where CaSR is involved.

The invention claimed is:

1. A glutamate compound represented by formula (I):

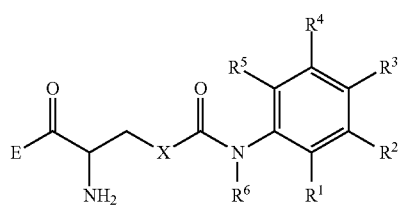

(I)

wherein:
$R^1$, $R^2$, $R^3$, $R^4$ and $R^5$ each independently represents a group selected from hydrogen atom, a halogeno group, hydroxyl group, nitro group, amino group, a $C_{1-6}$ alkyl group which may have a substituent(s), a $C_{1-6}$ alkoxy group which may have a substituent(s), a mono- or di-$C_{1-6}$ alkylamino group which may have a substituent(s), sulfo group, and a group:

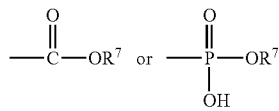

provided that at least one of $R^1$, $R^2$ and $R^3$ is sulfo group or a group selected from:

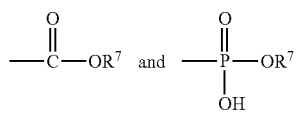

$R^6$ is hydrogen atom, hydroxyl group or a $C_{1-6}$ alkyl group which may have a substituent(s);
$R^7$ is hydrogen atom or a $C_{1-6}$ alkyl group which may have a substituent(s);
X is methylene group or oxygen atom; and,
E is a $C_{1-6}$ alkoxy group which may have a substituent(s), a mercapto group which may have a substituent(s), or a group:

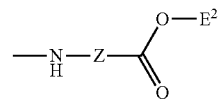

(IIb)

wherein in formula (IIb), Z represents a divalent $C_{1-6}$ hydrocarbon group which may have a substituent(s) and $E^2$ represents hydrogen atom or a $C_{1-6}$ alkyl group;
provided that:
when E is methoxy group, ethoxy group or benzyloxy group and X is methylene group, in a group:

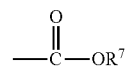

$R^7$ is not methyl group, ethyl group or benzyl group: and,
when E is butoxy group and X is methylene group, in a group:

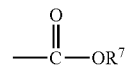

$R^7$ does not represent a group:

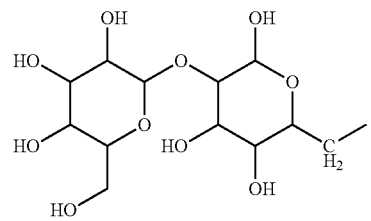

or a pharmaceutically acceptable salt thereof.

2. A glutamate compound represented by formula (I):

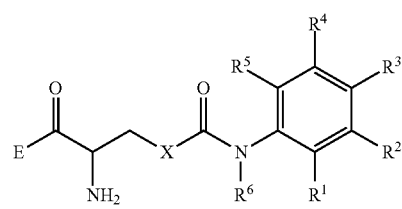

(I)

wherein:
$R^1$, $R^2$, $R^3$, $R^4$ and $R^5$ each independently represents a group selected from hydrogen atom, a halogeno group, hydroxyl group, nitro group, amino group, a $C_{1-6}$ alkyl group which may have a substituent(s), a $C_{1-6}$ alkoxy group which may have a substituent(s) or a mono- or di-$C_{1-6}$ alkylamino group which may have a substituent(s), sulfo group, and a group:

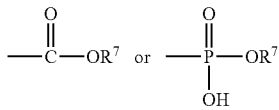

provided that at least one of $R^1$, $R^2$ and $R^3$ is sulfo group or a group selected from:

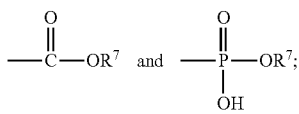

$R^6$ is hydrogen atom, hydroxyl group or a $C_{1-6}$ alkyl group which may have a substituent(s);

$R^7$ is hydrogen atom or a $C_{1-6}$ alkyl group which may have a substituent(s);

X is methylene group or oxygen atom; and,

E is a $C_{1-6}$ alkoxy group which may have a substituent(s), a mercapto group which may have a substituent(s), or a group;

(IIb)

wherein in formula (IIb), Z represents a divalent $C_{1-6}$ hydrocarbon group which may have a substituent(s) and $E^2$ represents hydrogen atom or a $C_{1-6}$ alkyl group;

provided that:

(i) when X is methylene group, $R^3$ is a carboxylic acid group and $R^1$, $R^2$, $R^4$, $R^5$ and $R^6$ are hydrogen atom, then, E is not methoxy group;

(ii) when X is methylene group, $R^2$ is a carboxylic acid group, $R^5$ is fluorine atom and $R^1$, $R^3$, $R^4$ and $R^6$ are hydrogen atom, then, E is not methoxy group; and, (iii) when E is methoxy group, ethoxy group or benzyloxy group and X is methylene group, then, in a group:

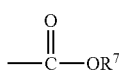

$R^7$ is not methyl group, ethyl group or benzyl group; and, when E is butoxy group and X is methylene group, in a group:

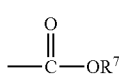

$R^7$ is not a group:

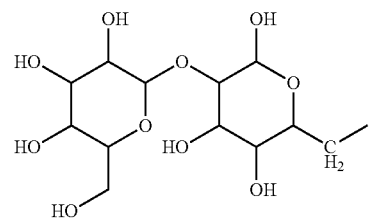

or a pharmaceutically acceptable salt thereof.

3. The glutamate compound of formula (I) or pharmaceutically acceptable salt thereof, according to any one of claims 1 and 2, wherein:

E is a $C_{1-6}$ alkoxy group or a group:

$$-OZ-E^1 \qquad \text{(IIa)}$$

wherein in formula (IIa), Z represents a divalent $C_{1-6}$ hydrocarbon group which may have a substituent(s), $E^1$ represents a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), or Z and $E^1$ may be combined together to form a ring.

4. The glutamate compound of formula (I) or pharmaceutically acceptable salt thereof, according to claim 1, wherein:

$R^1$, $R^3$, $R^4$ and $R^5$ each independently represents a group selected from hydrogen atom, a halogeno group, hydroxyl group, nitro group, amino group, a $C_{1-6}$ alkyl group which may have a substituent(s), a $C_{1-6}$ alkoxy group which may have a substituent(s), and a mono- or di-$C_{1-6}$ alkylamino group which may have a substituent(s):

$R^2$ represents sulfo group or a group selected from:

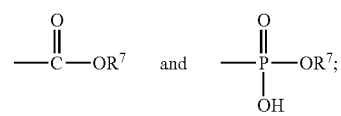

and, $R^6$ and $R^7$ each independently represents hydrogen atom or methyl group.

5. The glutamate compound of formula (I) or pharmaceutically acceptable salt thereof, according to claim 1, wherein:

$R^1$, $R^3$, $R^4$ and $R^5$ each independently represents a group selected from hydrogen atom, a halogeno group, hydroxyl group, nitro group, amino group, a $C_{1-3}$ alkyl group which may have a substituent(s), a $C_{1-3}$ alkoxy group which may have a substituent(s), and a mono- or di-$C_{1-3}$ alkylamino group which may have a substituent(s):

$R^2$ is sulfo group or a group selected from:

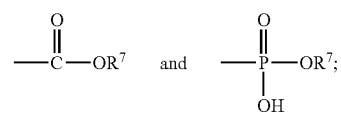

and, $R^6$ and $R^7$ each independently represents hydrogen atom or methyl group.

6. The glutamate compound of formula (I) or pharmaceutically acceptable salt thereof, according to claim 1, wherein:
$R^1$, $R^3$, $R^4$ and $R^5$ each independently represents a group selected from hydrogen atom, chloro or bromo group, hydroxyl group, nitro group, amino group, methyl group and methoxy group;
$R^2$ is sulfo group or a group selected from:

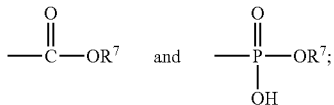

$R^6$ is hydrogen atom or methyl group;
$R^7$ is hydrogen atom; and,
X is methylene group.

7. The glutamate compound of formula (I) or pharmaceutically acceptable salt thereof, according to claim 1, wherein $R^2$ is sulfo group, a carboxylic acid group or a phosphonic acid group.

8. The glutamate compound of formula (I) or pharmaceutically acceptable salt thereof, according to claim 7, wherein $R^4$ is a halogeno group.

9. A pharmaceutical composition, comprising a glutamate compound or pharmaceutically acceptable salt thereof, according to claim 1.

10. A method for agonizing CaSR activity, comprising contacting CaSR with a glutamate compound
or a pharmaceutically acceptable salt thereof according to claim 1.

11. The method according to claim 10, wherein in formula (I):
E is a $C_{1-6}$ alkoxy group which may have a substituent(s), and said group is a group:

-OZ-E$^1$ (IIa)

wherein in formula (IIa), Z represents a divalent $C_{1-6}$ hydrocarbon group which may have a substituent(s), $E^1$ represents a $C_{1-6}$ acyloxy group which may have a substituent(s), a $C_{1-6}$ alkoxycarbonyloxy group which may have a substituent(s), an amino group which may have a substituent(s), carboxyl group, a $C_{1-6}$ alkoxycarbonyl group which may have a substituent(s), a halogen atom, an aryl group, a heteroaryl group, a $C_{1-6}$ alkoxy group which may have a substituent(s) or a carbamoyl group which may have a substituent(s), or Z and $E^1$ may be combined together to form a ring.

12. The pharmaceutical composition according to claim 9, which is a therapeutic agent for diseases improved by CaSR activation.

13. The glutamate compound of formula (I) or pharmaceutically acceptable salt thereof, according claim 2, wherein:
$R^1$, $R^3$, $R^4$ and $R^5$ each independently represents a group selected from hydrogen atom, a halogeno group, hydroxyl group, nitro group, amino group, a $C_{1-6}$ alkyl group which may have a substituent(s), a $C_{1-6}$ alkoxy group which may have a substituent(s), and a mono- or di-$C_{1-6}$ alkylamino group which may have a substituent(s):

$R^2$ represents sulfo group or a group selected from:

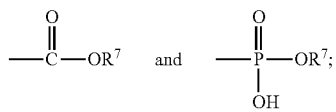

and,
$R^6$ and $R^7$ each independently represents hydrogen atom or methyl group.

14. The glutamate compound of formula (I) or pharmaceutically acceptable salt thereof, according to claim 2, wherein:
$R^1$, $R^3$, $R^4$ and $R^5$ each independently represents a group selected from hydrogen atom, a halogeno group, hydroxyl group, nitro group, amino group, a $C_{1-3}$ alkyl group which may have a substituent(s), a $C_{1-3}$ alkoxy group which may have a substituent(s), and a mono- or di-$C_{1-3}$ alkylamino group which may have a substituent(s):
$R^2$ is sulfo group or a group selected from:

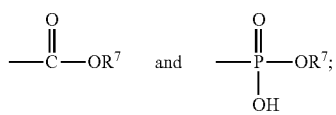

and,
$R^6$ and $R^7$ each independently represents hydrogen atom or methyl group.

15. The glutamate compound of formula (I) or pharmaceutically acceptable salt thereof, according to claim 2, wherein:
$R^1$, $R^3$, $R^4$ and $R^5$ each independently represents a group selected from hydrogen atom, chloro or bromo group, hydroxyl group, nitro group, amino group, methyl group and methoxy group;
$R^2$ is sulfo group or a group selected from:

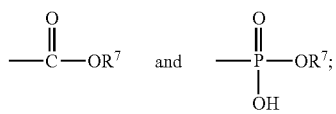

$R^6$ is hydrogen atom or methyl group;
$R^7$ is hydrogen atom; and,
X is methylene group.

16. The glutamate compound of formula (I) or pharmaceutically acceptable salt thereof, according to claim 2, wherein $R^2$ is sulfo group, a carboxylic acid group or a phosphonic acid group.

17. The glutamate compound of formula (I) or pharmaceutically acceptable salt thereof, according to claim 16, wherein $R^4$ is a halogeno group.

18. A pharmaceutical composition, comprising a glutamate compound or pharmaceutically acceptable salt thereof, according to claim 2.

* * * * *